US007355045B2

(12) United States Patent
Dey et al.

(10) Patent No.: US 7,355,045 B2
(45) Date of Patent: Apr. 8, 2008

(54) ISOTOPICALLY ENRICHED N-SUBSTITUTED PIPERAZINE ACETIC ACIDS AND METHODS FOR THE PREPARATION THEREOF

(75) Inventors: Subhakar Dey, Billerica, MA (US); Darryl J. C. Pappin, Boxborough, MA (US); Subhasish Purkayastha, Acton, MA (US); Sasi Pillai, Littleton, MA (US); James M. Coull, Westford, MA (US)

(73) Assignee: Applera Corporation, Framingham, MA (US)

( * ) Notice: Subject to any disclaimer, the term of this patent is extended or adjusted under 35 U.S.C. 154(b) by 792 days.

(21) Appl. No.: 10/751,387

(22) Filed: Jan. 5, 2004

(65) Prior Publication Data

US 2005/0148774 A1    Jul. 7, 2005

(51) Int. Cl.
*C07D 241/04* (2006.01)
(52) U.S. Cl. .................................................... 544/399
(58) Field of Classification Search ................. 544/399
See application file for complete search history.

(56) References Cited

U.S. PATENT DOCUMENTS

| | | | |
|---|---|---|---|
| 3,860,581 A | 1/1975 | Nudelman et al. ... | 260/293.3 D |
| 5,780,232 A | 7/1998 | Arlinghaus et al. ............ | 435/6 |
| 6,027,890 A | 2/2000 | Ness et al. ...................... | 435/6 |
| 6,156,527 A | 12/2000 | Schmidt et al. ............... | 435/24 |
| 6,312,893 B1 | 11/2001 | Van Ness et al. .............. | 435/6 |
| 6,319,476 B1 | 11/2001 | Victor, Jr. et al. .......... | 422/103 |
| 6,329,180 B1 | 12/2001 | Garvin ...................... | 435/91.2 |
| 6,403,309 B1 | 6/2002 | Iris et al. ...................... | 435/6 |
| 6,428,956 B1 | 8/2002 | Crooke et al. ................. | 435/6 |
| 6,472,156 B1 | 10/2002 | Wittwer et al. ................ | 435/6 |
| 6,613,508 B1 | 9/2003 | Ness et al. ..................... | 435/6 |
| 6,629,040 B1 | 9/2003 | Goodlett et al. .............. | 702/23 |
| 6,750,061 B2 | 6/2004 | Chait et al. .................... | 435/89 |
| 6,824,981 B2 | 11/2004 | Chait et al. | |
| 7,045,296 B2 | 5/2006 | Parker et al. | |
| 2002/0119456 A1 | 8/2002 | Ness et al. ..................... | 435/6 |
| 2003/0077595 A1 | 4/2003 | Van Ness et al. .............. | 435/6 |
| 2005/0049406 A1 | 3/2005 | Lerchen et al. | |

FOREIGN PATENT DOCUMENTS

| | | |
|---|---|---|
| EP | 0209763 | 7/1986 |
| EP | 0261804 | 8/1987 |
| EP | 1027454 | 1/1998 |
| EP | 0990047 | 7/1998 |
| JP | 01125357 A2 | 5/1989 |
| WO | WO94/15944 | 7/1994 |
| WO | WO98/15648 | 12/1996 |
| WO | WO97/11958 | 4/1997 |
| WO | WO98/31830 | 6/1998 |
| WO | WO98/32876 | 7/1998 |
| WO | WO99/05319 | 5/1999 |
| WO | WO00/11208 | 3/2000 |
| WO | WO01/68664 | 9/2001 |
| WO | WO01/86296 | 11/2001 |
| WO | WO02/14867 | 2/2002 |
| WO | WO03/001206 | 1/2003 |
| WO | WO03/025576 | 3/2003 |
| WO | WO03/040288 | 5/2003 |
| WO | WO03/077851 | 9/2003 |
| WO | WO2004/086050 | 10/2004 |

OTHER PUBLICATIONS

Aebersold, R. et al. "Mass Spectrometry in Proteomics". Chem Rev. 101, 269-298 (2001).
Al-Shahrour, F. et al. "FatiGO: A Web Tool For Finding Significant Associations of Gene Ontology Terms With Groups of Genes (fatigo.bioinfo.cnio.es)". Bioinformatics, 20, 578-580 (2004).
Alving, K. et al. "Characterization of O-Glycosylation Sites in MUC2 Glycopeptides by NanoElectrospray QTOF Mass Spectrometry". Journal of Mass Spectrometry, 34, 395-407 (1999).
Anderegg, R. et al. "Mass Spectrometric Characterization of a Protein-Ligand Interaction". J. Am. Chem. Soc., 117, 1374-1377 (1995).
Banks, R.E. et al. "Evidence for the existence of a novel pregnancy-associated soluble variant of the vascular endothelial growth factor receptor, Flt-1", Molecular Human Reproduction, 4, 377-386 (1998).
Bates, G. et al, Selective and Direct Activation of O-Esters. Conversion of Phenyl and 2,2,2-Trifluoroethyl Esters Into Acyl Imidazolides. Tetrahedron Letters, 49, 4423-4426 (1976).
Beck-Sickinger, A. et al. "Epitope mapping: synthetic approaches to the understanding of molecular recognition in the immune system". Pharmaceutical ACTA Helvetiac, 68, 3-20 (1993).
Benard, P. et al. "Homogeneous Multiplex Genotyping of Hemochromatosis Mutations with Fluorescent Hybridization Probes", American Journal of Pathology, 4, 1055-1061 (1998).
Biemann, K. et al. "Primary Structure of Peptides and Proteins". Biological Mass Spectrometry, 275-297 (1994).
Biswas, A. et al, "Rearrangement of N-(p-Toluenesulfonyloxy-2-Pyrrolidinone". Heterocycles, 11, 2849-2851 (1987).
Chase B.H. et al, "The Synthesis of C-Labelled Diethylcarbamazine, 1-Diethylcarbamyl/-4-methylpiperazine("Hetrazan")". The Journal of The Chemical Society, 3874-3877 (1953).
Chu, Y. et al. "Affinity Capillary Electrophoresis-Mass Spectrometry for Screening Combinatorial Libraries". J. Am. Chem. Soc. 118, 7827-7835 (1996).

(Continued)

*Primary Examiner*—James O. Wilson
*Assistant Examiner*—Ebenezer Sackey
(74) *Attorney, Agent, or Firm*—Orrick, Herrington & Sutcliffe

(57) ABSTRACT

In some embodiments, this invention pertains to isotopically enriched N-substituted piperazine acetic acids. In some embodiments, this invention pertains to methods for the preparation of isotopically enriched N-substituted piperazine acetic acids.

26 Claims, 11 Drawing Sheets

OTHER PUBLICATIONS

Chu, Y. et al. "Free Solution Identification of Candidate Peptides from Combinatorial Libraries by Affinity Capillary Electrophoresis/Mass Spectrometry". J. Am. Chem. Soc. 117, 5419-5420 (1995).

Chu, Y. et al. "Using Affinity Capillary Electrophoresis To Identify the Peptide in a Peptide Library that Binds Most Tightly to Vancomycin". J. Org. Chem. 58, 648-652 (1993).

Cotterill, L. et al. "Qa-1 interaction and T cell regognition of the Qa-1 determinant modifier peptide". Eur. J. Immunol,- 27, 2123-2132 (1997).

Dunayevskiy, Y. et al, "Application of capillary electrophoresis-electrospray ionization mass spectrometry in the determination of molecular diversity". Proc. Natl. Acad. Sci. USA, 93, 6152-6157 (1996).

Ecker, D. et al. "Combinatorial Drug Discovery: Which Methods Will Produce the Greatest Value?" Biotechnology, 13,351-360 (1995).

Eng, J. et al. " An Approach to Correlate Tandem Mass Spectral Data of Peptides With Amino Acid Sequences in a Protein Database". J. Am. Soc. Mass Spectrom., 5, 976-989 (1994).

Epton, R. "Peptides. Synthesis. Solid Phase Methods". Innovation and Perseptives in Solid Phase Synthesis. 57-63 (1990).

Fatica, A. et al. " Making Ribosomes". Curr. Opin. Cell Biol., 14, 313-318 (2002).

Gao, J. et al. "Screening Derivated Peptide Libraries for Tight Binding Inhibitors to Carbonic Anhydrase II by Electrospray Ionization-Mass Spectrometry." J. Med. Chem. 39, 1949-1955 (1996).

Geysen, H. et al. "Isotope or mass encoding of combinatorial libraries". Chemistry & Biology, 3, 679-688.(1996).

Gerber, S.A. et al. "Absolute Quantification of Proteins and Phosphoproteins From Cell Lysates by Tandem MS". Proc. Natl. Acad. Sci., 100, 6940-6945 (2003).

Goodlett, D. et al. "Reduced Elution Speed Detection for Capillary Electrophoresis/Mass Spectrometry". J. Microl Sep, 5, 57, 62 (1993).

Gonzalez, C.I. et al. " Nonsense-mediated mRNA Decay in Saccharomyces cerevisiae". Gene, 274, 15-25 (2001).

Goshe, M.B. et al. "Stable Isotope-Coded Proteomic Mass Spectrometry". Curr Opin Biotechnol., 14, 101-109 (2003).

Griffin, T.J. et al. " Complementary Profiling of Gene Expression at the Transcriptome and Proteome Levels in Saccharomyces cerevisiae". Mol. Cell Proteomics, 1, 323-333 (2002).

Gygi, S.P. et al. "Correlation Between Protein and mRNA Abundance In Yeast". Mol. Cell Biol., 19, 1720-1730 (1999).

Gygi S.P. et al. "Quantitative Analysis of Complex Protein Mixtures Using Isotope-Coded Affinity Tags". Nat. Biotechnol., 17, 994-999 (1999).

Ham, S. et al. "HLA-DO is a negative modulator of HLA-DM-mediated MHC class II peptide loading". Current Biology, 7, 950-957 (1997).

Han, D.K. et al. "Quantitative Profiling of Differentiation-induced Microsomal Proteins Using Isotype-Coded Affinity Tags and Mass Spectrometry". Natl. Biotechnol., 19, 946-951 (2001).

Hanley, S. et al. "Re-evaluation of the primary structure of Ralstonia eutropha phasing and implifications for polyhydroxyalkanoic acid granule binding". FEBS Letters, 447, 99-105 (1999).

Harris et al. "An Improved Synthesis of 1-Methyl-2,5-piperazinedione". J. Heterocyclic Chem. 18, 423-424 (1981).

He, F. et al. Genome-Wide Analysis of mRNA's Regulated by the Nonsense-mediated and 5' to 3' mRNA Decay Pathways in Yeast. Mol. Cell, 12, 1439-1452 (2003).

Henion, J. et al. "Mass Spectrometric Investigations of Drug-Receptor Interactions". Therapeutic Drug Monitoring, 15, 563-569 (1993).

Henry, N.L. et al, Purification and Characterization of Yeast RNA Polymerase II General Initiation Factor g. J. Biol. Chem. 267, 23388-23392 (1992).

Hentze, M.W. et al. "A Perfect Message: RNA Surveillance And Nonsense-Mediated Decay". Cell, 96, 307-310 (1999).

Hermanson, G. et al. "The Chemistry of Reactive Groups". Bioconjugate Techniques, Chapter 2, 137-165.

Heyes, M. et al. "($^{18}$O) Quinolinic Acid: Its Esterification without Back Exchange for Use as Internal Standard in the Quantification of Brain and CSF Quinolinic Acid".

Höss, M. et al. "A human DNA editing enzyme homologous to the Escherichia coli DnaQ/MutD protein". The EMBO Journal, 18, 3868-3875 (1999).

Hughs, I. Et al. "Design of Self-Coded Combinatorial Libraries To Facilitate Direct Analysis of Ligands by Mass Spectrometry". J. Med. Chem., 41, 3804-3811 (1998).

Hsu, C. et al. Yeast cells lacking 5'-3' Exoribonuclease I Contain mRNA Species That are Poly (A) Deficient and Partially Lack The 5' Cap Structure. Mol. Cell. Biol., 13, 4826-4835 (1993).

Ibarrola, N. et al. A Novel Proteomic Approach For Specific Identification of Tyrosine Kinase Substrates Using 13C-Labeled Tyrosine. J. Biol. Chem. In press (2004).

Ju, Q. et al. "REB1, a Yeast DNA-Binding Protein With Many Targets, is Essential For Growth and Bears Some Resemblance to the Oncogene myb". Mol. Cell Biol., 10, 5226-5234 (1990).

Jung, g. et al. "Multiple Peptide Synthesis Methods and Their Applications". Angewandte Chemie, 31, 367-486 (1992).

Karimi-Busheri, F. et al. "Molecular Characterization of a Human DNA Kinase". The Journal of Biological Chemistry, 274, 24187-24194 (1999).

Kondo, H. et al. "p47 is a cofactor for p97-mediated membrane fusion". Nature, 388, 75-78 (1997).

Köster, H. et al. "A strategy for rapid and efficient DNA sequencing by mass spectrometry", Nature Biotechnology, 14, 1123-1128 (1996).

Krusic, P. et al. "Electron Spin Resonance Studies of Fluoroalkyl Radicals in Solution. III. Photolysis of Perfluoroketones and Adduct Formation". The Journal of Physical Chemistry, 78, 2036-2041 (1974).

Kurihara, T. et al. "Sec24p and Iss1p Function Interchangeably in Transport Vesicle Formation From The Endoplasmic Reticulum in Saccharomyces cerevisiae". Mol. Biol. Cell, 11, 983-998 (2000).

Maderazo, A.B. et al. "Upflp Control of Nonsense mRNA Translation is Regulated by Nmd2p and Upf3p". Mol. Cell Biol., 20, 4591-4603 (2000).

Mak, M. et al, "Stability of Asp-Pro Bond Under High and Low Energy Collision Induced Dissociation Conditions in the Immunodominant Epitope Region of Herpes Simplex Virion Glycoprotein D". Rapid Commun. Mass Spectrom, 12, 837-842 (1998).

Mangus, D.A. et al. "Pbp 1, A Factor Interacting With Saccharomyces cerevisiae Poly(A)-Binding Protein, Regulates Polyadenylation". Mol. Cell Biol. 18, 7383-7396 (1998).

Martinovic S. et al. "Selective Incorporation of Isotopically Labeled Amino Acids For Identification of Intact Proteins on a Proteome-Wide Level". J. Mass Spectrom., 37, 99-107 (2002).

Masselon, C. et al. "Accurate Mass Multiplexed Tandem Mass Spectrometry for High-Throughput Polypeptide Identification from Mixtures". Anal. Chem., 72, 1918-1924 (2000).

Metzger, J. et al. "Analytical methods for the characterization of synthetic peptide libraries". Peptides, 481-482 (1992).

Metzger, J. et al. "Electrospray Mass Spectrmetry and Tandem Mass Spectrometry of Synthetic Multicomponent Peptide Mixtures: Determination of Composition and Purity". Analytical Biochemistry, 219, 261-277 (1994).

Metzger, J. et al. "Ion-Spray Mass Spectrometry and High-Performance Liquid Chromatography-Mass Spectrometry of Synthetic Peptide Libraries". Agnew. Chem. Int. Ed. Engl., 6, 894-896 (1993).

Moore, R. et al. "A Microscale Electrospray Interface Incorporating a Monolithic, Poly(styrene-divinylbenzene) Support for On-Line Liquid Chromatography/Tandem Mass Spectrometry Analysis of Peptides and Proteins". Anal. Chem. 70, 4879-4884 (1998).

Nawrocki, J. et al, "Analysis of Combinational Libraries Using Electrospray Fourier Transform Ion Cyckotron Resonance Mass Spectrometry". Rapid Communication in Mass Spectrometry, 10, 1860-1864 (1996).

Nazarpack-Kandlousy, N. et al. "Regiochemical Tagging: A New Tool for Structural Characterization of Isomeric Components in Combinatorial Mixtures". J. Am. Chem. Soc., 122, 3358-3366 (2000).

Needels M. et al. "Generation and screening of an oligonucleotide-encoded synthetic peptide library". Proc. Natl. Acad. Sci. USA, 90, 10700-10704 (1993).

Nestler, H. et al. "A General Method for Molecular Tagging of Encoded Combinatorial Chemistry Libraries". J. Org. Chem, 59, 4723-4724 (1994).

Nikolaiev, V. et al. "Peptide-Encoding For Structure Determination of Nonsequence-able Polymers Within Libraries Synthesized and Tested on Solid-Phase Supports". Peptide Research, 3, 161-170, (1994).

Nutiu, R. et al. "Tripartite Molecular Beacons". Nucleic Acids Research, 18, 1-9 (2002).

Ohlmeyer, M. et al. "Complex synthetic chemical libraries indexed with molecular tags". Proc. Natl. Acad. Sci, USA, 90, 10922-10926 (1993).

Olejnik, J. et al. "Photocleavable biotin phosphoramidite for 5'-end labeling, affinity purification and phosphorylation of synthetic oligonucleotides". Nucleic Acids Research, 24, 361-366 (1996).

Olejnik, J. et al. "Photocleavable peptide-DNA conjugates: synthesis and applications to DNA analysis using MALDI-MS". Nucleic Acids Research, 23, 4626-4631 (1999).

Ong, S.E. et al. "Properties of 13C-Substituted Arginine in Stable Isotope Labeling By Amino Acids In Cell Culture (SILAC)". J. Proteome Res. 2, 173-181 (2003).

Ong, S.E. et al. "Stable Isotope Labeling By Amino Acids In Cell Culture SILAC, as a Simple And Accurate Approach to Expression Proteomics". Mol. Cell Proteomics, 1, 376-386 (2002).

Parker, K.C. et al. "Depth of Proteome Issues: A Yeast ICAT Reagent Study". Mol. Cell Proteomics, In Press (2004).

Pitha, J. et al. " Synthetic Analogs of Nucleic Acids". Biomedical Polymers, 271-297 (1980).

Perkins, D.N. et al. "Probability-Based Protein Identification By Searching Sequence Databases Using Mass Spectrometry Data". Electrophoresis, 20, 3551-3567 (1999).

Peterson, C.L. et al. "Characterization of the Yeast Swl1, SWI2, and SWI3 Genes, Which encode a Global Activator of Transcription". Cell, 68, 573-583 (1992).

Przybylski, M. et al, " Mass spectrometric approaches to molecular characterization of protein-nucleic acid interactions". Toxicology Letters, 82/83, 567-575 (1995).

Qiu, Y. et al. "Acid-Labile Isotope-Coded Extractants: A Class of Reagents for Quantitative Mass Spectrometric Analysis of Complex Protein Mixtures". Analytical Chemistry, 19, 4969-4979.

Rao, T. et al, TFA-NHS as bifunctional protecting agent: simultaneous protection and activation of amino carboxylic acids. Tetrahedron Letters, 43, 7793-7795 (2002).

Rautio, J. et al. "Synthesis And In Vitro Evaluation Of Novel Morpholinyl- and Methylpiperazinylacyloxyalkyl Prodrugs of 2-(6-Methoxy-2-naphthyl)propionic Acid (Naproxen) for Topical Drug Delivery". J. Med. Chem., 115, 1489-1494 (2000).

Ross, C. et al. "Two Dimensional Fourier Transform Ion Cyclotron Resonance Mass Spectrometry/Mass Spectrometry with Stored-Waveform Ion Radius Modulation". J. Am. Chem. Soc., 115, 7854-7861 (1993).

Sadler, I. et al. " A Yeast Gene Important For Protein Assembly Into the Endoplasmic Reticulum and the Nucleus Has Homology to Dnaj, an *Escherichia Coli* Heat Shock Protein". J. Cell Biol. 109, 2665-2675 (1989).

Saghatelian, A. et al. "DNA Detection and Signal Amplification via an Engineered Allosteric Enzyme". J. Am. Chem. Soc. 125, 344-345 (2003).

Sakakibara S. et al., "A New Reagent For The P-Nitrophenylation of Carboxylic Acids". Bulletin of The Chemical Society of Japan, 8, 1231-1232 (1964).

Sakakibara, S. et al., "The Trifluoroacetate Method of Peptide Synthesis I. The Synthesis and Use of Trifluoroacetate Reagents". The Synthesis and Use of Trifluoroacetate Reagents, 11, 1979-1983 (1965).

Schröter, M. et al. "Genotyping of Hepatitis C Virus Types 1,2,3 and 4 by a One-Step LightCycler Method Using Three Different Pairs of Hybridization Probes". Journal of Clinical Microbiology, 6, 2046-2050 (2002).

Shevchenko, A. et al. "MALDI Quadrupole Time-of-Flight Mass Spectrometry: A Powerful Tool for Proteomic Research". Anal. Chem., 72, 2132-2141 (2000).

Shevchenko, A. et al. " Rapid 'de Novo' Peptide Sequencing By a Combination of Nanoelectrospray, Isotopic Labeling and a Quadrupole/Time-of-Flight Mass Spectrometer". Rapid Comm. In Mass Spectro., 11, 1015-1024 (1997).

Sickinger, A. et al. "Epitope mapping: synthetic approaches to the understanding of molecular regognition in the immune system". Pharmaceutical ACTA Helvetiac, 68, 3-20 (1993).

Stacey, M. et al, "A General Method of Esterification Using Trifluoracetic Anhydride", Nature, 8, 705.

Stevanovic, S. et al. "Multiple Sequence Analysis: Pool Sequencing of Synthetic and Natural Peptide Libraries". Analytical Biochemistry, 212, 212-220 (1993).

Stevanovic, S. et al. " Natural and Synthetic Peptide Pools: Characterization by Sequencing and Electrospray Mass Spectrometry". Bioorganic & Medical Chemistry Letters, 3, 431-436 (1993).

Stevens, A. et al. " Fragments of the Internal Transcribed Spacer 1 or Pre-rRNA Accumulate in *Saccharomyces cerevisiae* lacking 5'-3' Exoribonuclease 1". J. Bacteriol, 173, 7024-7028 (1991).

Tao, W.A. et al. "Advances in Quantitative Proteomics Via Stable Isotope Tagging and Mass Spectrometry". Curr Opin Biotechnol., 14, 110-118 (2003).

Thomas, D. et al. "Y SAM2 Encodes The Second Methionine S-Adenosyl Transferase in *Saccharomyces cerevisiae*: Physiology and Regulation of Both Enzymes". Mol. Cell Biol., 8, 5132-5139 (1998).

Thompson, A. et al. "Tandem Mass Tags: A Novel Quantification Strategy for Comparative Analysis of Complex Protein Mixtures by MS/MS". Anal. Chem, 75, 1895-1904 (2003).

Tugal, T. et al. "The Orc4p and Orc5p Subunits of the *Xenopus* and the Human Origin Recognition Complex Are Related to Orc1p and Cdc6p". Journal of Biological Chemistry, 49, 32421-32429 (1998).

Veenstra, T. et al. "Proteome Analysis Using Selective Incorporation of Isotopically Labeled Amino Acids". American Soc. For Mass. Spect., 11, 78-82 (2000).

Wagner, D. et al. "Ratio Encoding Combinatorial Libraries with Stable Isotopes and their Utility in Pharmaceutical Research" Combinational Chemistry & High Throughput Screening, 3, 143-153 (1998).

Washburn, M.P. et al. "Reproducibility of Quantiative Proteomic Analyses of Complex Biological Mixtures by Multidimensional Protein Identification Technology". Anal. Chem., 75, 5054-5061 (2003).

Wentworth, P. et al. " Generating and analyzing combinatorial chemistry libraries". Analytical Chemistry, 9, 109-115 (1998).

Wegierski, T. et al. Bms1p, a G-domain-containig protein, Associates with Rcl1p and is Required For 18S rRNA Biogenesis in Yeast. RNA, 7, 1254-1267 (2001).

Weiboldt, R. et al. "Immunoaffinity Ultrafiltration with Ion Spray HPLC/MS for Screening Small-Molecule Libraries". Analytical Chemistry, 69, 1683-1691 (1997).

Williams, E. et al. "Hadamard Transform Measurement of Tandem Fourier-Transform Mass Spectra". Anal. Chem. 62, 698-703 (1990).

Winger, B. et al. "Characterization of Combinatorial Peptide Libraries by Electrospray Ionization Fourier Transform Mass Spectrometry". Rapid Comm. In Mass Spectrometry. 10, 1811-1813 (1996).

Wissner, A. et al, "Reaction of tert-Butyldimethylsilyl Esters with Oxalyl Chloride-DimethylformideL Preparation of Carboxylic Acid Chlorides Under Neutral Conditions". J. Org. Chem. 43, 3972-3974 (1978).

Yates, J.R. "Mass Spectrometry From genetics To Proteomics". TIG, 16, 5-8 (2000).

Yates, J.R. "Database Searching Using Mass Spectrometry Data". Electrophoresis, 19, 893-900 (1998).

Yates, N.E et al. "A novel N-terminal derivative designed to simplify peptide fragmentation". Proceedings of the 43rd ASMS Conference of Mass Spectrometry and Allied Topics, Atlanta, Georgia (May 21-26) (1996).

Young, J.D. et al. "Thymosin β 4 sulfoxide is an anti-inflammatory agent generated by monocytesin the presence of glucocorticoids". Nature Medicine, 12, 1424-1427.

Young, P. et al. "Alternative Mobile Phases For Enhanced HPLC Peptide Mapping". Millipore Bioforum, 4, (1993).

Zhang, X. et al. "B=N-Terminal peptide labeling strategy for incorporation of isotopic tags: a method for the determination of site-specific absolute phosphorylation stoichiometry". Rapid Comm. In Mass Spec., 16, 2325-2332 (2002).

Zhong, T. et al. The Yeast SIS 1 Protein, a DnaJ Homolog, is Required For The Initiation of Translation. *Cell*, 73, 1175-1186 (1993).

Zhou, H. et al. "Quantitive proteome analysis by solid-phase isotype tagging and mass spectrometry". Nature Biotechnology, 19, 512-515 (2002).

PCT International Search Report and Written Opinion mailed Aug. 10, 2006.

Bartlett Jones, M., et al., "Peptide Ladder Sequencing by Mass Spectrometry Using a Novel, Volatile Degradation Reagent", Rapid Communications in Mass Spectrometry, vol. 8, 737-742 (1994).

Day, Richard et al, "N-Terminal Groups in Mass Spectrometry of Peptides. A Study Including Some New and Useful Derivatives", J. Org. Chem., vol. 38, No. 4, 1975 782-788.

Golding, Bernard T. et al. "Chemistry of Nitrogen Mustard [2-Chloro-N0 (2-chloroethyl) -N-methylethanamine] studied by Nuclear Magnetic Resonance Spectroscopy", J. Chem Soc. Perkin Trans. II 1987, pp. 705-713.

Huang, Yulin et al, "A Method for High Efficiency Peptide Sequencing Using Combined Enzymatic Digestion and Chemical Derivatization on MALDI MSMS", Applied Biosystems Poster No. 1159.

Ross, Philip et al, "Investigation of Chemical Derivatization for Peptide CID Using LC-MALDI TOF MS/MS", Applied Biosystems Poster No. ThPF 250.

Roth, Kenneth et al, "Charge Derivatization of Peptides for Analysis by Mass Spectrometry", Mass Spectrometry Reviews, 1998, 17, 255-274.

Sherman, Nicholas et al, "Novel N-Terminal Derivative Designed to Simplify Peptide Fragmentation", Proceedings of the 43rd ASMS Conference on Mass Spectrometry and Allied Topics, Atlanta, Georgia, May 21-26, 1995, pp. 626-627.

Shetty, Umesha H. et al, "Piperazine Ring Cleavage in the Electron Impact Induced Fragmentation of Piperazine Type Phenothiazine Antipsychotic Agents", Biomedical Mass Spectrometry, vol. 10, No. 11, 1983, pp. 601-607.

PCT/US2005/00023 International Search Report.

Malawska et al., "Structure-Activity Relationship Studies of New N-Substituted Amides of $\alpha$-Piperazine-$\gamma$-Hydroxybutyric Acid as Active Anticonvulsants", Arch Pharm Pharm Med Chem, vol. 330, 1997, pp. 91-99.

Rautio, J. et al. "Synthesis and in Vitro Evaluation of Novel Morpholinyl- and Methylpiperazinylacyloxyalkyl Prodrugs of 2-(6-Methoxy-2-naphthyl_ propionic Acid (naproxen) for Topical Drug Delivery", J Med Chem, vol. 43, No. 8, Apr. 20, 2000, pp. 1489-1494.

Scheme For The Synthesis Of N-Methyl Piperazine

Scheme A For The Synthesis Of N-Methyl Piperazine Acetic Acids

Scheme B For The Synthesis Of N-Methyl Piperazine Acetic Acids

Scheme C For The Synthesis Of N-Methyl Piperazine Acetic Acids

Scheme A For The Synthesis Of $^{18}$O Labeled N-Methyl Piperazine Acetic Acids

Scheme B For The Synthesis Of $^{18}$O Labeled N-Methyl Piperazine Acetic Acids

Scheme A For The Synthesis Of Various Active Esters Of N-Methyl Piperazine
Via Imidazolide Formation Scheme B For The Synthesis Of Various Active Esters Of N-Methyl Piperazine Via Oxallyl Chloride Scheme C For The Synthesis Of Various Active Esters Of N-Methyl Piperazine Via Trifluoroacetate Ester Scheme For The Synthesis Of Various Active Esters Of N-Methyl Piperazine Via Trifluoroacetate Esters Isotopic Pathway For Prepared N-Methyl Piperazine Acetic Acids

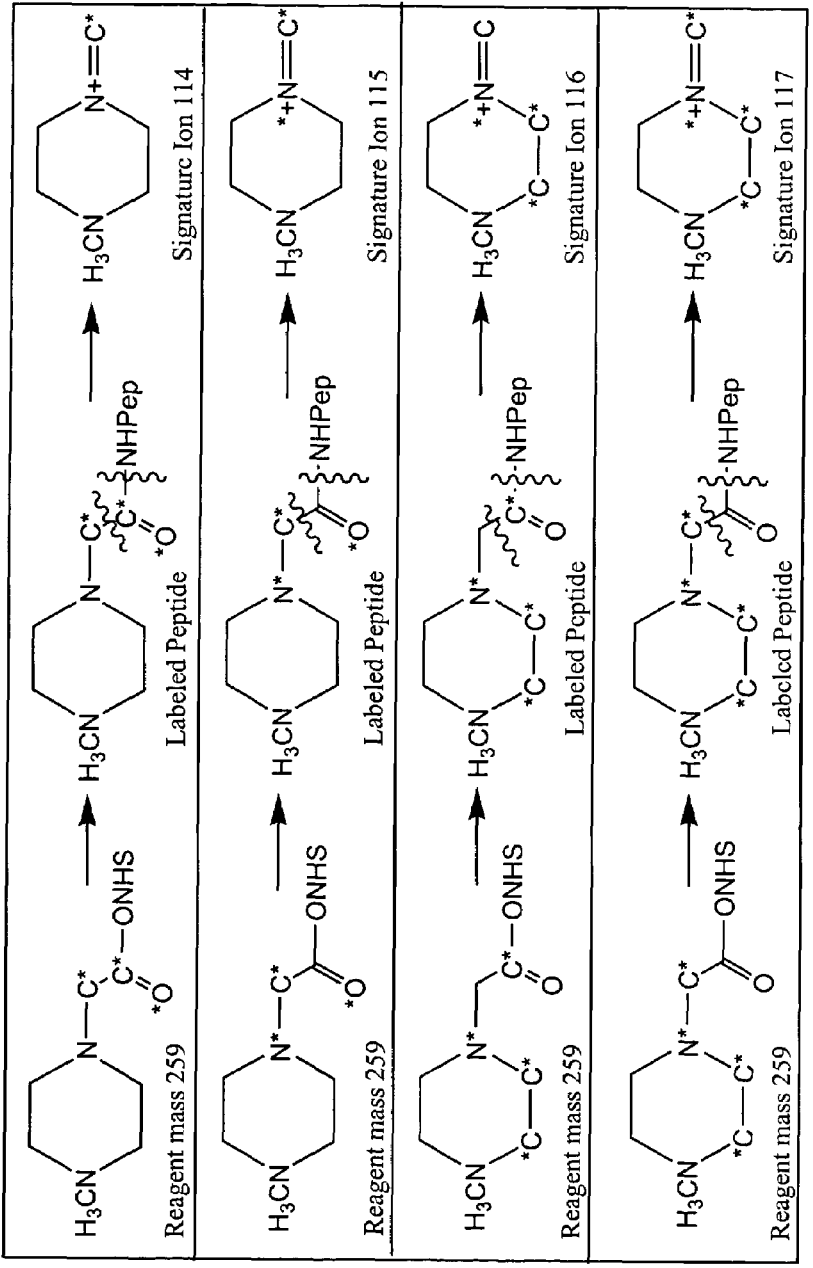

ISOTOPICALLY ENRICHED N-SUBSTITUTED PIPERAZINE ACETIC ACIDS AND METHODS FOR THE PREPARATION THEREOF

CROSS REFERENCE TO RELATED APPLICATIONS

This application is related to U.S. Ser. No. 10/751,388 entitled: "Isotopically Enriched N-Substituted piperazines And Methods For The Preparation Thereof" and filed on this Jan. 5, 2004, incorporated herein by reference. This application is related to U.S. Ser. No. 10/751,354 entitled: "Active Esters Of N-Substituted piperazine Acetic Acids, Including Isotopically Enriched Versions Thereof" and filed on this Jan. 5, 2004, incorporated herein by reference. This application is related to U.S. Ser. No. 10/751,353 entitled: "Mixtures Of Isobarically Labeled Analytes And Fragments Ions Derived Therefrom" and filed on this Jan. 5, 2004, incorporated herein by reference.

FIELD OF THE INVENTION

In some embodiments, this invention pertains to isotopically enriched N-substituted piperazine acetic acids. In some embodiments, this invention pertains to methods for the preparation of isotopically enriched N-substituted piperazine acetic acids.

Introduction

In some embodiments, this invention pertains to isotopically enriched N-substituted piperazine acetic acids. In some embodiments, this invention pertains to methods for the preparation of isotopically enriched N-substituted piperazine acetic acids. N-substituted piperazine acetic acids can be intermediates in the preparation of active esters of N-substituted piperazine acetic acid. Active esters are well known in peptide synthesis and refer to certain esters that are easily reacted with an amine of an amino acid under conditions commonly used in peptide synthesis (For a discussion of active esters please see: Innovation And Perspectives In Solid Phase Synthesis, Editor: Roger Epton, SPCC (UK) Ltd, Birmingham, 1990).

The active esters of N-substituted piperazine acetic acid can be used as labeling reagents. In some embodiments, a set of isobaric labeling reagents can be prepared. The set of isobaric labeling reagents can be used to label analytes, such as peptides, proteins, amino acids, oligonucleotides, DNA, RNA, lipids, carbohydrates, steroids, small molecules and the like. The labeled analytes can be mixed together and analyzed simultaneously in a mass spectrometer. Because the heavy atom isotope distribution in each of the isobaric labeling reagents can be designed to result in the generation of a unique "signature ion" when analyzed in a mass spectrometer (MS), labeled components of the mixture associated with each of the labeling reagents, and by implication components of each labeling reaction used to produce the mixture, can be deconvoluted. Deconvolution can include determining the relative and/or absolute amount of one or more labeled components in each of the individual samples that were labeled and combined to form the mixture. The N-substituted piperazine acetic acid active esters described herein therefore can be powerful tools for analyte analysis, including but not limited to multiplex proteomic analysis.

BRIEF DESCRIPTION OF THE DRAWINGS

FIG. 5B is an illustration of the labeling and fragmentation of peptides using four isobaric N-methyl piperazine acetic acid active ester labeling reagents.

DEFINITIONS

Figure 1:
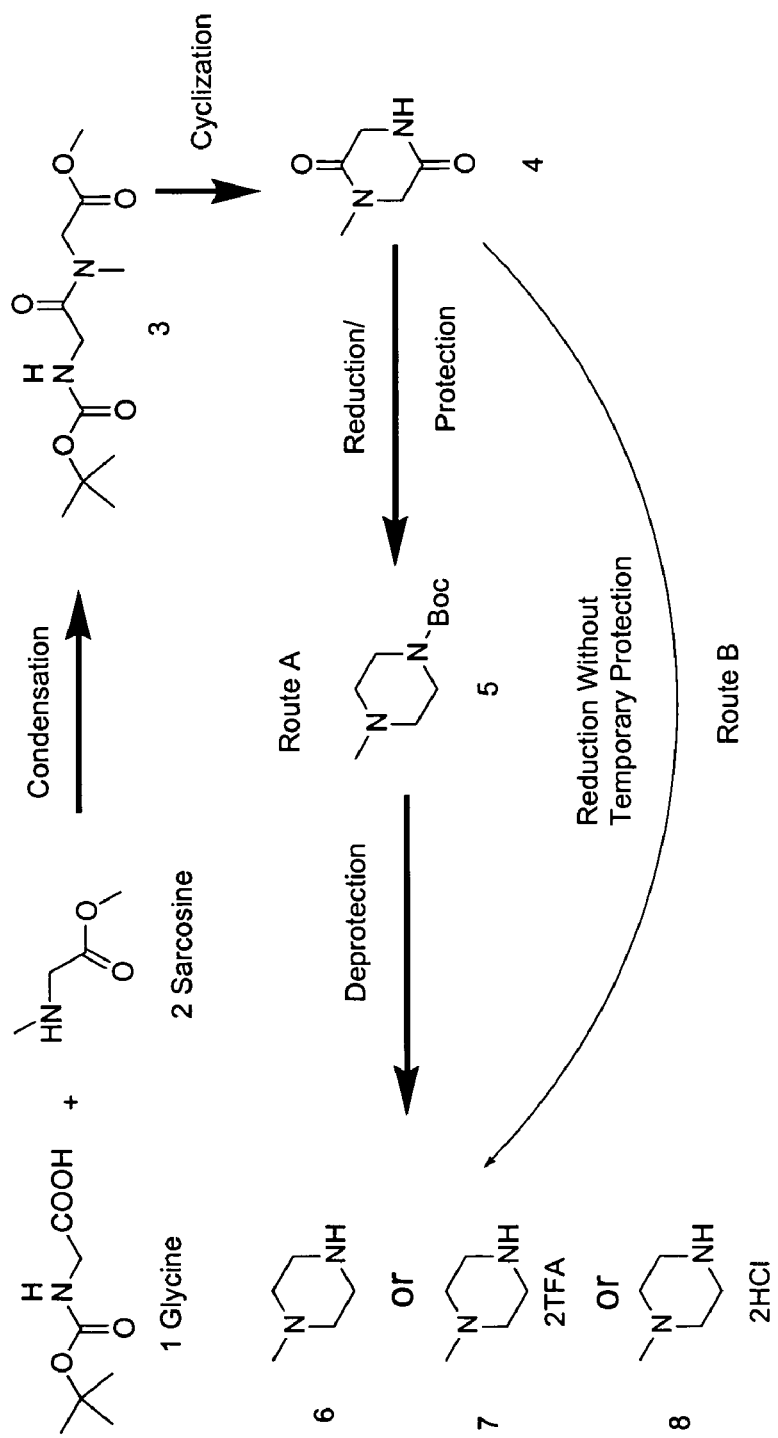
FIG. 1 is an illustration of a synthetic scheme for the synthesis of N-methyl piperazines.

For the purposes of interpreting of this specification, the following definitions will apply and whenever appropriate, terms used in the singular will also include the plural and vice versa:

As used herein, "analyte" refers to a molecule of interest that may be determined. Non-limiting examples of analytes include, but are not limited to, proteins, peptides, nucleic acids (both DNA or RNA), carbohydrates, lipids, steroids and other small molecules with a molecular weight of less than 1500 Daltons (Da). The source of the analyte, or the sample comprising the analyte, is not a limitation as it can come from any source. The analyte or analytes can be natural or synthetic. Non-limiting examples of sources for the analyte, or the sample comprising the analyte, include cells or tissues, or cultures (or subcultures) thereof. Non-limiting examples of analyte sources include, but are not limited to, crude or processed cell lysates, body fluids, tissue extracts, cell extracts or fractions (or portions) from a separations process such as a chromatographic separation, a 1D electrophoretic separation, a 2D electrophoretic separation or a capillary electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the cell lysate with a proteolytic enzyme to thereby digest precursor peptides and/or proteins.

Except as when clearly not intended based upon the context in which it is being used (e.g. when made in reference to a structure that dictates otherwise), "ester" refers to both an ester and/or a thioester.

As used herein, "fragmentation" refers to the breaking of a covalent bond.

As used herein, "fragment" refers to a product of fragmentation (noun) or the operation of causing fragmentation (verb).

As used herein, "isotopically enriched" means that a compound (e.g. labeling reagent) has been enriched synthetically with one or more heavy atom isotopes (e.g. stable isotopes such as Deuterium, $^{13}C$, $^{15}N$, $^{18}O$, $^{37}Cl$ or $^{81}Br$). Because isotopic enrichment is not 100% effective, there can be impurities of the compound that are of lesser states of enrichment and these will have a lower mass. Likewise, because of over-enrichment (undesired enrichment) and because of natural isotopic abundance, there can be impurities of greater mass.

As used herein, "labeling reagent" refers to a moiety suitable to mark an analyte for determination. The term label is synonymous with the terms tag and mark and other equivalent terms and phrases. For example, a labeled analyte can be referred to as a tagged analyte or a marked analyte.

As used herein, "natural isotopic abundance" refers to the level (or distribution) of one or more isotopes found in a compound based upon the natural prevalence of an isotope or isotopes in nature. For example, a natural compound obtained from living plant matter will typically contain about 0.6% $^{13}C$.

Description of Various Embodiments of the Invention

I. Preparation of N-Substituted Piperazines Comprising Heavy Atom Isotopes

In some embodiments, this invention pertains to a method for the production of isotopically enriched N-substituted piperazines, and the N-substituted piperazines themselves. According to the method, a partially protected amino acid can be condensed with an N-substituted amino acid ester wherein at least one of the two amino acids comprises a heavy atom isotope such as, for example, $^{18}O$, $^{15}N$, $^{13}C$, $^{81}Br$, $^{37}Cl$ or deuterium. When condensing the two amino acids, any side chain reactive groups can be protected as they would be for the condensation of amino acids to form peptides. Similarly, the condensation chemistry can be chosen from the various methods known for condensing amino acids. These include, but are not limited to, the use of carbodiimides (e.g. dicyclohexylcarbodiimide, DCC), active esters, mixed anhydride formation and the like.

The partially protected amino acid comprises an amine-protecting group (N-protecting group), such as tert-butyloxycarbonyl (t-boc); a well-known protecting group in peptide synthesis. The partially protect amino acid can comprise a side chain protecting where the amino acid comprises a reactive side chain moiety. The amino acid can be any natural amino acid (e.g. glycine, alanine, lysine) or non-natural amino acid of basic structure:

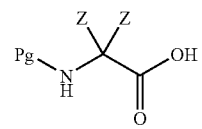

wherein Pg can be the N-protecting group. Each group Z can be independently hydrogen, deuterium, fluorine, chlorine, bromine, iodine, an amino acid side chain, a straight chain or branched C1-C6 alkyl group that may optionally contain a substituted or unsubstituted aryl group wherein the carbon atoms of the alkyl and aryl groups each independently comprise linked hydrogen, deuterium or fluorine atoms, a straight chain or branched C1-C6 alkyl ether group that may optionally contain a substituted or unsubstituted aryl group wherein the carbon atoms of the alkyl and aryl groups each independently comprise linked hydrogen, deuterium or fluorine atoms or a straight chain or branched C1-C6 alkoxy group that may optionally contain a substituted or unsubstituted aryl group wherein the carbon atoms of the alkyl and aryl groups each independently comprise linked hydrogen, deuterium or fluorine atoms. In some embodiments, each Z is independently hydrogen, methyl or methoxy. In some embodiments, each Z is hydrogen, deuterium, fluorine, chlorine, bromine or iodine. An alkyl ether group, as used herein, can include one or more polyethylene glycol substituents. Similarly, the alkoxy group, as used herein, can comprise ether and/or polyethylene glycol substituents. The N-protecting group can be an acid labile protecting group. The N-protecting group can be a base labile protecting group.

The N-substituted amino acid ester can be any natural amino acid (e.g. glycine, alanine, lysine) or non-natural amino acid of basic structure:

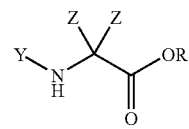

wherein Z is previously defined above. The group Y can be a straight chain or branched C1-C6 alkyl group or a straight chain or branched C1-C6 alkyl ether group wherein the carbon atoms of the alkyl group or alkyl ether group each independently comprise linked hydrogen, deuterium or fluorine atoms. In some embodiments, Y is methyl, ethyl, n-propyl, isopropyl, n-butyl, isobutyl, sec-butyl or tert-butyl. The group R can be a straight chain or branched C1-C6 alkyl group or a substituted or unsubstituted phenyl group, wherein the carbon atoms of the alkyl group or phenyl group each independently comprise linked hydrogen, deuterium or fluorine atoms. In some embodiments, the N-substituted amino acid ester is the ester (e.g. methyl or ethyl) of sarcosine, which is an ester of N-methyl glycine.

Every possible permutation of $^{15}N$ or $^{13}C$ labeled glycine is commercially available. Likewise, other natural amino acids are commercially available with one or more incorporated heavy atom isotopes. Because glycine, and other amino acids, comprising one or more heavy atom isotopes are commercially available, these amino acids can be easily incorporated into the procedure for the production of N-substituted piperazines. The amino acids comprising heavy atom isotopes can be N-protected using procedures well-known in peptide chemistry. For example, the amino acids can be N-protected with a 9-fluorenylmethoxycarbonyl (Fmoc) group or a t-boc group. Furthermore the amino acids comprising heavy atom isotopes can be N-alkylated and converted to an ester of the amino acid using well-known procedures. Accordingly, heavy atom isotope containing starting materials for the preparation of N-substituted piperazines, as described herein, are either commercially available, or can be easily prepared from commercially available amino acids using no more than routine experimentation.

According to the method, the two amino acids can be condensed to thereby produce an N-protected peptide dimer as an ester. The N-protected peptide dimer ester can comprise one or more heavy atom isotopes via the incorporation of the one or more amino acids comprising one or more heavy atom isotopes. The N-protected peptide dimer ester can comprise one heavy atom isotope, two heavy atom isotopes, three heavy atom isotopes, four heavy atom isotopes, five heavy atom isotopes or six heavy atom isotopes. The N-protected peptide dimer ester can have the general formula:

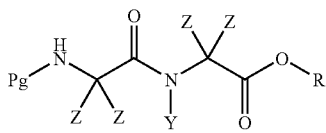

wherein Pg, R, Y and Z are previously defined.

According to the method, the N-protected peptide dimer ester can then be cyclized to form a 6-membered cyclic dione. Cyclization proceeds by removing the N-protecting group of the N-protected peptide dimer ester and driving the reaction of the deprotected amine with the ester group. The reaction can be carried out under basic conditions and can be heated to speed production of the product. The product of the cyclization can have the general formula:

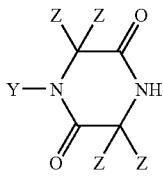

wherein Y and Z are previously defined.

According to the method, the ketone groups of the cyclic dione can then be reduced to form the desired N-substituted piperazine comprising one or more heavy atom isotopes. The reduction can be performed using a reducing agent, such as lithium aluminum hydride (LAH) or Red-Al (Sigma-Aldrich). The product, in some embodiments being a volatile oil, can be optionally temporarily modified (e.g. protected) to aid in isolation. Because piperazine comprises two basic nitrogen atoms, the product can, in some embodiments, be isolated as a mono or bis-acid salt. For example, the N-substituted piperazine comprising one or more heavy atom isotopes can be isolated as a mono-TFA salt, a mono-HCl salt, a bis-TFA salt or a bis-HCl salt.

FIG. 1 illustrates the application of the aforementioned general procedure to the production of N-methyl piperazine. Examples 1-4 describe the application of the illustrated procedure to the production of three different N-methyl piperazines each comprising 1-3 heavy atom isotopes.

With reference to FIG. 1 and Examples 1-4, t-boc protected glycine (1) is condensed with sarcosine methyl ester (2) to thereby produce the dipeptide (3). The t-boc group is removed and the dipeptide is cyclized to the cyclic dione (4). The ketone groups of the dione are then reduced to produce N-methyl piperazine. The N-methyl piperazine product can either be transiently protected (5) or can be obtained directly from the reduction (6). The product can also be obtained as a salt (e.g. TFA salt (7) or HCl (8)) of an acid.

In summary, a wide variety of N-substituted piperazine compounds, unlabeled or labeled with one or more heavy atom isotopes, can be produced by the aforementioned process. Consequently, the present invention contemplates all possible isotopically enriched N-substituted piperazine compound comprising one or more heavy atom isotopes of the general formula:

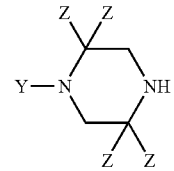

including all possible salt forms thereof, wherein Y and Z are previously defined.

II. Preparation of N-Substituted Piperazine Acetic Acids Comprising Heavy Atom Isotopes In some embodiments, this invention pertains to methods for the production of isotopically enriched N-substituted piperazine acetic as well as the isotopically enriched N-substituted piperazine acetic acids. In some embodiments, an N-substituted piperazine can be reacted with a halo acetic acid moiety comprising one or more heavy atom isotopes. In this context, halo refers to the halogens, chlorine, bromine and iodine. In still some other embodiments, an N-substituted piperazine comprising one or more heavy atom isotopes can be reacted with a halo acetic acid moiety. In some other embodiments, an N-substituted piperazine comprising one or more heavy atom isotopes can be reacted with a halo acetic acid moiety comprising one or more heavy atom isotopes. Accordingly, the heavy atom isotopes found in the product N-substituted piperazine acetic acids can be introduced by way of the piperazine, by way of the halo acetic acid moiety or by way of both the piperazine and the halo acetic acid moiety. As will be discussed in more detail below, $^{18}O$ can also be introduced into the carboxylic acid moiety of an N-substituted piperazine acetic acid by way of exchange with $H_2^{18}O$.

Numerous light (by light we mean that the compound is not isotopically enriched with one or more heavy atom isotopes) N-substituted piperazines (e.g. N-methyl and N-ethyl piperazine) are commercially available. Furthermore, Section I above describes the preparation of N-substituted piperazine comprising one or more heavy atoms from commercially available amino acids. Both light and heavy (by heavy we mean that the compound has been isotopically enriched with one or more heavy atom isotopes) N-substituted piperazine can be used to produce the N-substituted piperazine acetic acids comprising one or more heavy atom isotopes.

Numerous light and heavy halo acetic acid moieties are commercially available. The halo acetic acid moiety to be reacted with the N-substituted piperazine can be purchased as the carboxylic acid or as an ester of the carboxylic acid (e.g. the methyl ester, ethyl ester or phenyl ester). If only the carboxylic acid is available and the ester is desired, the ester can be prepared using well-known esterification methods. If only the ester is available and the carboxylic acid is desired, the ester can be hydrolyzed to produce the carboxylic acid. Either the carboxylic acid or the ester can be used in the alkylation reaction provided that an additional equivalent of base is required if the carboxylic acid is used. If the ester is used to perform the alkylation, the product ester can be hydrolyzed to produce the N-substituted piperazine acetic acid. General structures for the carboxylic acid and the ester compounds that can be used to alkylate N-substituted piperazines are:

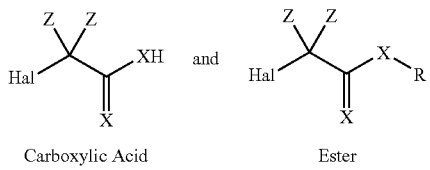

Carboxylic Acid        Ester wherein Z and R are defined above. Hal is a halogen (Cl, Br or I) and X is oxygen (O) or sulfur (S). In some embodiments, X is $^{16}O$ or $^{18}O$. One or more of the atoms of the halo acetic acid compound can be a heavy atom isotope.

The alkylation of an N-substituted piperazine with a halo acetic acid moiety proceeds under basic conditions. The base need only be strong enough to deprotonate piperazine but can be selected to not substantially react with the halo acetic acid moiety. In some embodiments, two or more equivalents of N-substituted piperazine can be used, as N-substituted piperazine is a base. If it is desirable to use only one equivalent of N-substituted piperazine (for example, when the N-substituted piperazine is labeled with one or more heavy atom isotopes and is therefore valuable), other bases can be used. Suitable bases include, but are not limited to, hindered bases such as triethylamine ($Et_3N$) and diisopropylethyamine (DIEPA). Other suitable bases in sodium carbonate and potassium carbonate. Hindered bases are a good choice because they do not react substantially with the halo acetic acid moiety.

Figure 2A:
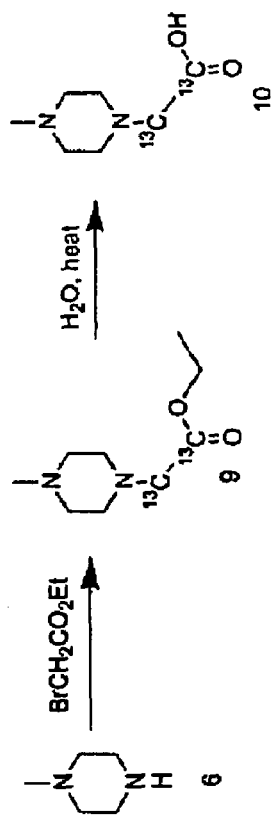
FIG. 2A is an illustration of a synthetic scheme for the synthesis of N-methyl piperazine acetic acids.
Figure 2B:
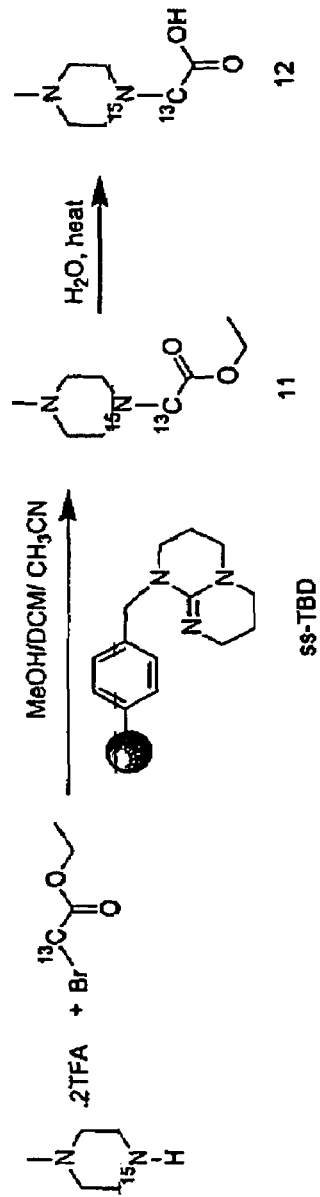
FIG. 2B is an illustration of another synthetic scheme for the synthesis of N-methyl piperazine acetic acids.

A solid phase base, such as 1,5,7-Triazabicyclo[4.4.0]dec-5-ene (TBD) bound to polystyrene crosslinked with 2% DVB, Capacity (base): ~2.6 mmol/g (ss-TBD, Fluka, P/N 90603) can also be used (See FIG. 2B). A solid phase base has the advantage that it is easily, and completely, removed from the product by filtration once the alkylation reaction has been completed. Accordingly, the resulting product is not contaminated with salt of the base.

If the carboxylic acid is used to alkylate the N-substituted piperazine, the reaction can produce a product of the general formula:

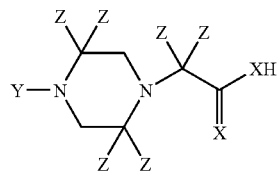

or a salt thereof, wherein X, Y and Z have been previously defined. One or more atoms of the N-substituted piperazine acetic acid can be a heavy atom isotope.

If the ester is used to alkylate the N-substituted piperazine, the reaction will produce an ester of the general formula:

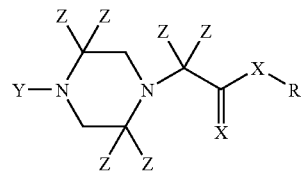

or a salt thereof, wherein R, X, Y and Z have been previously defined. One or more atoms of the N-substituted piperazine acetic acid ester can be a heavy atom isotope. The N-substituted piperazine acetic acid ester can be converted to the N-substituted piperazine acetic acid of general formula:

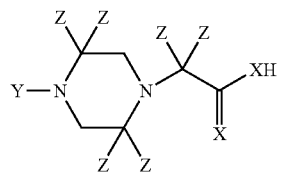

by hydrolysis of the ester. Depending on the state of protonation of the ester, it may or may not be necessary to and base to aqueous solution to perform the hydrolysis because piperazine is basic (unless neutralized by acid). Accordingly, base can be added as required to induce the hydrolysis of the ester to the carboxylic acid, but in some embodiments it will not be required. Hydrolysis can also be performed under aqueous acidic conditions.

N-substituted piperazine acetic acid is zwitterionic. Because it comprises a carboxylic acid group (or thio acid group) and two basic nitrogen atoms, it can exist in at least four different forms. It can exist completely deprotonated as its carboxylate anion. It can exist as its mono protonated zwitterion. It can exist as a monobasic salt (e.g. mono-TFA or mono-HCl salt). It can also exist as its dibasic salt (e.g. bis-TFA or bis-HCl salt). The state of protonation of the product is a function of the conditions under which it was isolated. All protonation states of N-substituted piperazine acetic acid are contemplated as embodiments of the present invention.

With reference to FIGS. 2A and 2B, as well as Examples 5 and 6, respectively, the production of two different isotopically enriched N-methyl piperazine acetic acid compounds is described. In FIG. 2A and Example 5, two equivalents of commercially available unlabeled N-methyl piperazine is reacted with ethyl bromoacetate to produce a N-methyl piperazine acetic acid compound comprising two $^{13}C$ atoms. Because N-methyl piperazine is basic, hydrolysis of the ethyl ester proceeded by merely heating the compound in an aqueous solution.

With reference to FIG. 2B and Example 6, the starting piperazine is a bis-TFA salt of $^{15}N$ labeled N-methyl piperazine. Acid salts of the piperazine base can be alkylated so long as sufficient base is added to the reaction to deprotonate piperazine. In this example, the ethyl bromoacetate is $^{13}C$ labeled. Because both the piperazine and acetic acid reactants comprise heavy atom isotopes, a solid phase base was chosen so that only one equivalent of each reactant was required to produce the product. As was observed with Example 5, hydrolysis of the ethyl ester proceeded by mere heating the compound in an aqueous solution.

In some other embodiments, the N-substituted piperazine acetic acid can be assembled on a solid support. According to the method and with reference to FIG. 2C, the halo acetic acid moiety, as a carboxylic acid, can be reached with trityl chloride resin to thereby produce a support bound halo acetic acid. The support bound halo acetic acid can then be treated with the desired N-substituted piperazine (e.g. N-methyl piperazine) under basic conditions to thereby produce the N-substituted piperazine acetic acid. Isotopically enriched N-methyl piperazine and halo acetic acid moieties can be used, including $^{18}O$ labeled compounds although $^{18}O$ labeling can involve special considerations and is discussed in more detail below.

In accordance with the aforementioned discussion, a heavy atom isotope can be incorporated at virtually any position of the N-substituted piperazine acetic acid, including $^{18}O$ incorporation that will be discussed in more detail below. Consequently, the present invention contemplates all possible isotopically enriched N-substituted piperazine acetic acids comprising one or more heavy atom isotopes of the general formula:

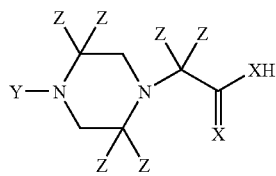

including all possible salt forms thereof.

III. Incorporation of $^{18}O$ into N-Substituted Piperazine Acetic Acids

In some embodiments, this invention pertains to methods for the incorporation of $^{18}O$ into N-substituted piperazine acetic acids as well as to the $^{18}O$ labeled N-substituted piperazine acetic acids themselves. In some embodiments, incorporation of $^{18}O$ is not substantially different as compared with the methods described for the preparation of isotopically labeled N-substituted piperazine acetic acids in Section II, above. In some other embodiments, incorporation of $^{18}O$ is substantially different and takes advantage of the very caveat that creates some concern about the methods previously discussed.

The caveat with respect to the preparation of $^{18}O$ labeled N-substituted piperazine acetic acids lies with the exchange of $^{18}O \Leftrightarrow ^{16}O$ that can occur between unlabeled water $(H_2^{16}O)$ and the $^{18}O$ of a heavy carboxylic acid group. A carboxylic acid group is inherently acidic. Acid can catalyze the exchange of the oxygen atoms of a carboxylic acid group and water, such as residual water in a sample or water used in a reaction (e.g. hydrolysis of an ester). Consequently, whenever $^{18}O$ labeled N-substituted piperazine acetic acids were desired, one of two different synthetic routes was chosen.

In some embodiments, the $^{18}O$ labeled N-substituted piperazine acetic acid was obtained by alkylation with an appropriately $^{18}O$ labeled halo acetic acid moiety. The procedure is essentially as outlined in Section II, above except that an acid labile ester of the halo acetic acid was used in the alkylation reaction. In some embodiments, the halo acetic acid moiety comprised the formula:

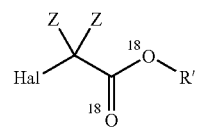

wherein Hal is previously defined and R' is an acid labile ester group, including but not limited to tert-butyldimethylsilyl or t-boc.

Figure 3A:
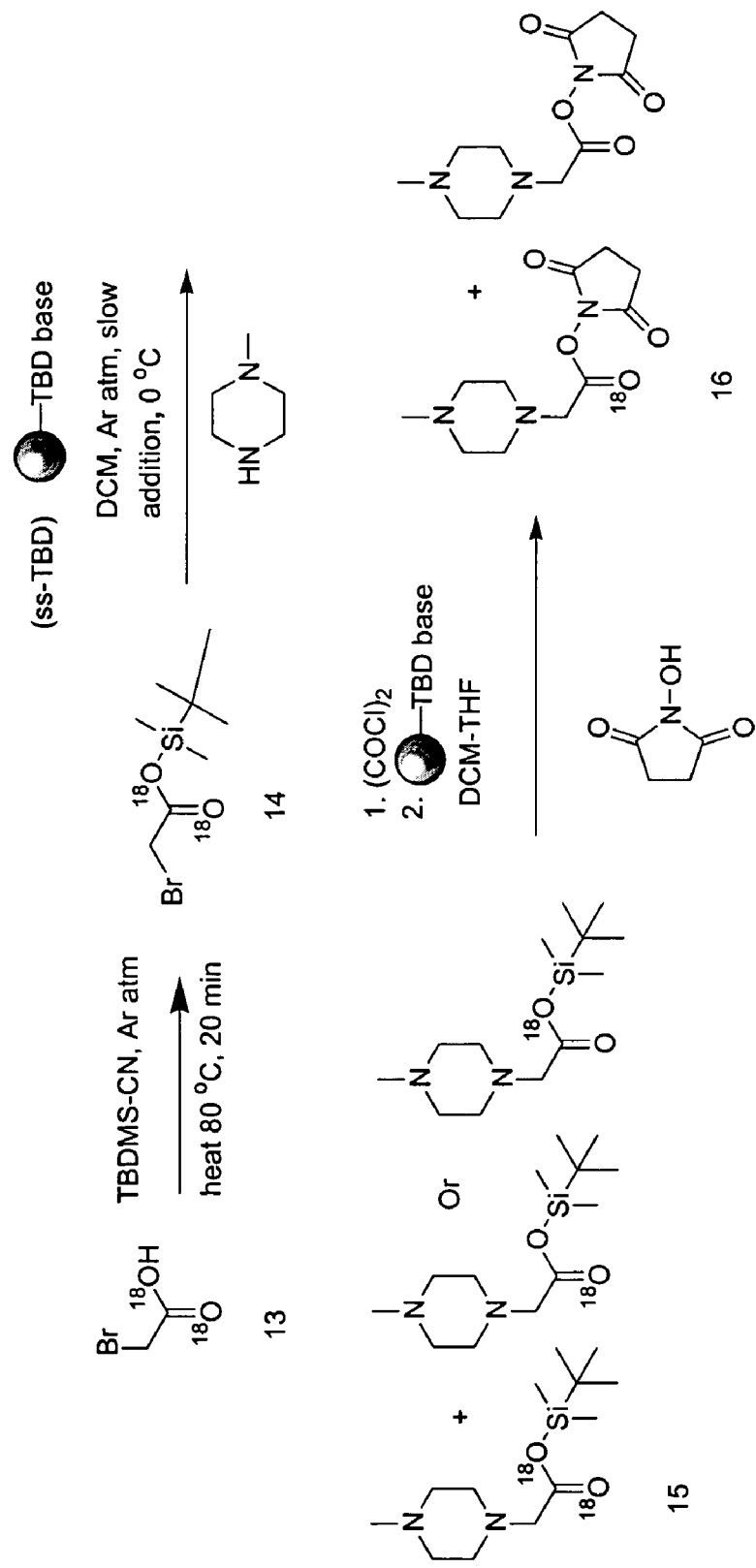
FIG. 3A is an illustration of a synthetic scheme for the synthesis of $^{18}O$ labeled N-methyl piperazine acetic acids.

With reference to FIG. 3A and Example 8, the tert-butyldimethylsilyl (TBDMS) ester of $(^{18}O)_2$ bromoacetic acid (14) was used in the alkylation reaction. This ester was prepared using $^{18}O$ labeled bromoacetic acid (13), obtained as a custom order from Cambridge Isotope Laboratory, Inc., and TBDMS-CN. The TBDMS ester of N-methyl piperazine acetic acid (15) was the product of the alkylation with N-methyl piperazine. The TBDMS ester was selected so that it could be converted to the acid chloride with, for example, oxalyl chloride thereby avoiding the requirement for any water and the possible exchange of $^{18}O$ with $^{16}O$. In the presence of solid phase base (ss-TBD) and N-hydroxysuccinimide (NHS), the acid chloride was converted to the NHS ester (16). If the carboxylic acid is desired, instead of the active ester, the TBDMS ester could be converted to the carboxylic acid by treatment with an anhydrous acid such as TFA. Accordingly, aqueous treatment that might lead to $^{18}O$ $^{16}O$ exchange, can be avoided whether the active ester or the carboxylic acid is desired.

Figure 3B:
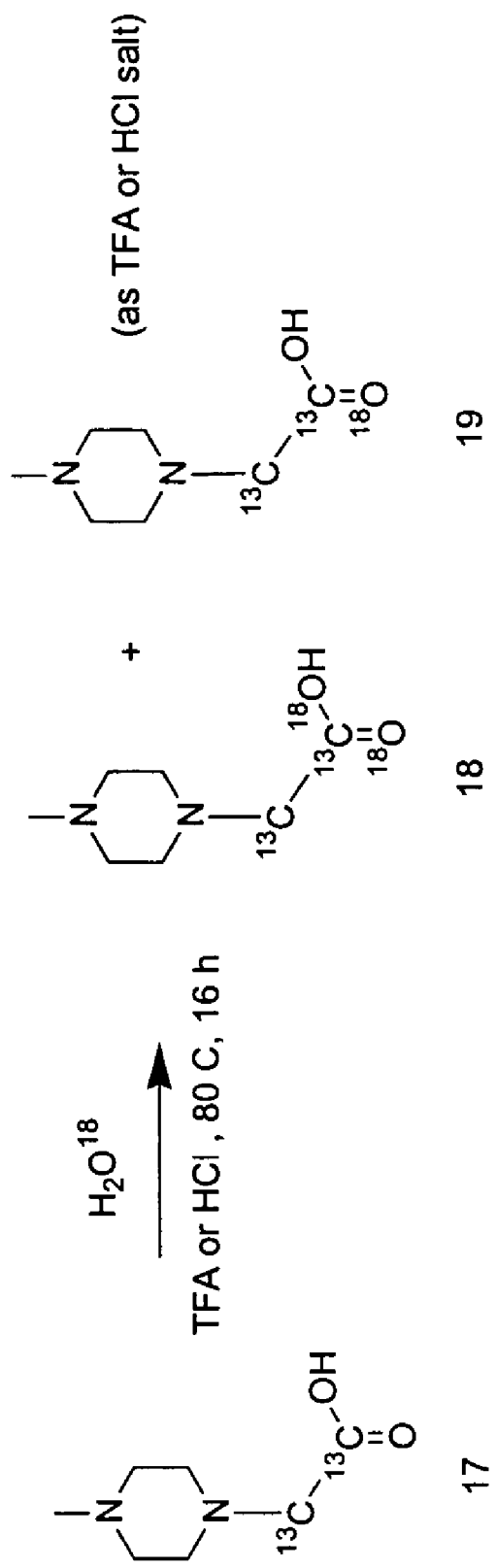
FIG. 3B is an illustration of another synthetic scheme for the synthesis of $^{18}O$ labeled N-methyl piperazine acetic acids.

In some other embodiments, the alkylation to produce N-substituted piperazine acetic acid proceeded as described in Section II, above and the $^{18}O$ was later incorporated. With reference to FIG. 3B and Example 9, it was found that $^{18}O$ could be incorporated into the carboxylic acid group of any N-substituted piperazine acetic acid by treatment of the N-substituted piperazine acetic acid with $H_2^{18}O$ under acidic conditions. For example and with reference to FIG. 3B, an isotopically enriched N-methyl piperazine acetic acid (17) lacking $^{18}O$, used to produce the 114 labeling reagent, was treated with $H_2^{18}O$ and either HCl or TFA to thereby produce the TFA or HCl salt of the $^{18}O$ isotopically enriched N-methyl piperazine acetic acid (18) and (19).

Furthermore, the isotopic purity of the product could be increased by repeated cycles of treatment with $H_2^{18}O$ under acidic conditions. The higher the state of enrichment of the $H_2^{18}O$, the fewer cycles required to produce highly $^{18}O$ enriched N-substituted piperazine acetic acid. When $H_2^{18}O$ of 99% purity was used, the isotopic enrichment of N-substituted piperazine acetic acid was typically 96% after two cycles. Because this exchange was performed under acidic conditions, the product was easily isolated as the bis-acid salt of N-substituted piperazine acetic acid (e.g. the bis-TFA or bis-HCl salt).

Consequently, the present invention contemplates all possible isotopically enriched N-substituted piperazine acetic acids comprising one or more heavy atom isotopes of the general formula:

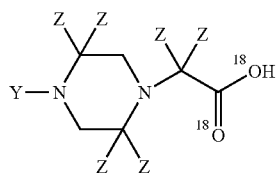

including all possible salt forms thereof.

IV. Preparation of Various Active Esters of N-Substituted Piperazine Acetic Acid In some embodiments, this invention pertains to methods for the preparation of active esters of N-substituted piperazine acetic acid, including isotopically enriched versions thereof, as well as the N-substituted piperazine acetic acid esters themselves, and isotopically enriched versions thereof. The active ester can be any active ester. In some embodiments, the active ester can be formed using an alcohol or thiol of the following formula:

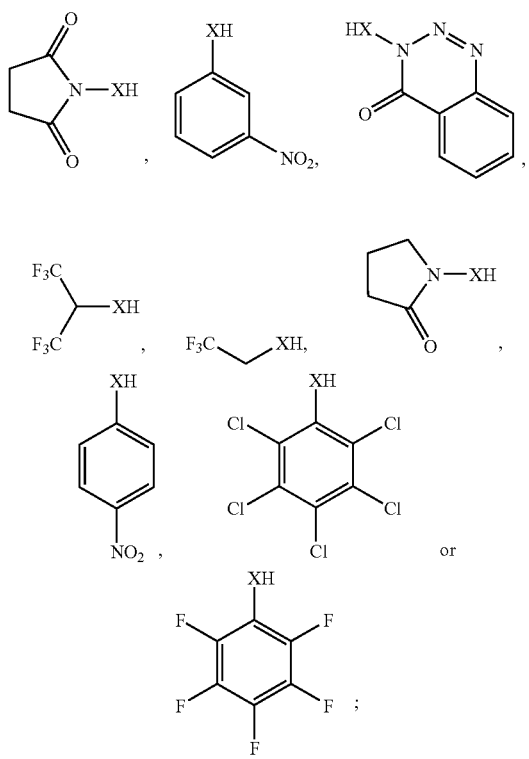

wherein X is O or S, but preferably O. In some other embodiments, the active ester can be formed using an alcohol or thiol of the following formula:

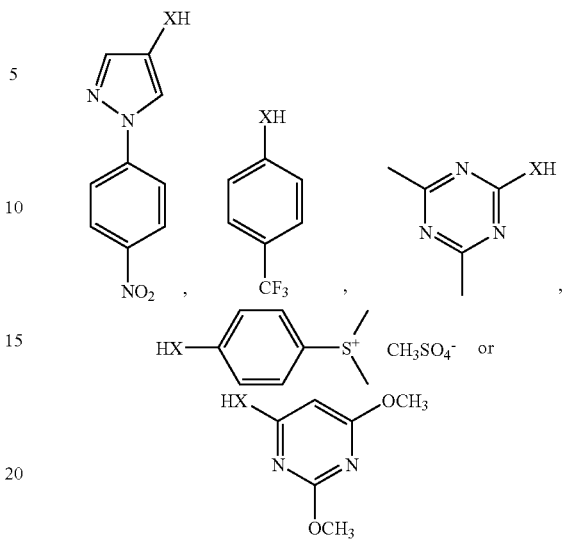

wherein X is O or S, but preferably O.

In some embodiments, the active ester can be prepared through an intermediary imidazolide. According to this method, an N-substituted piperazine acetic acid ester, including isotopically enriched versions thereof, can be converted to the imidazolide. The imidazolide so prepared can then be reacted with the alcohol of choice to thereby produce the active ester of the selected alcohol.

Figure 4A:
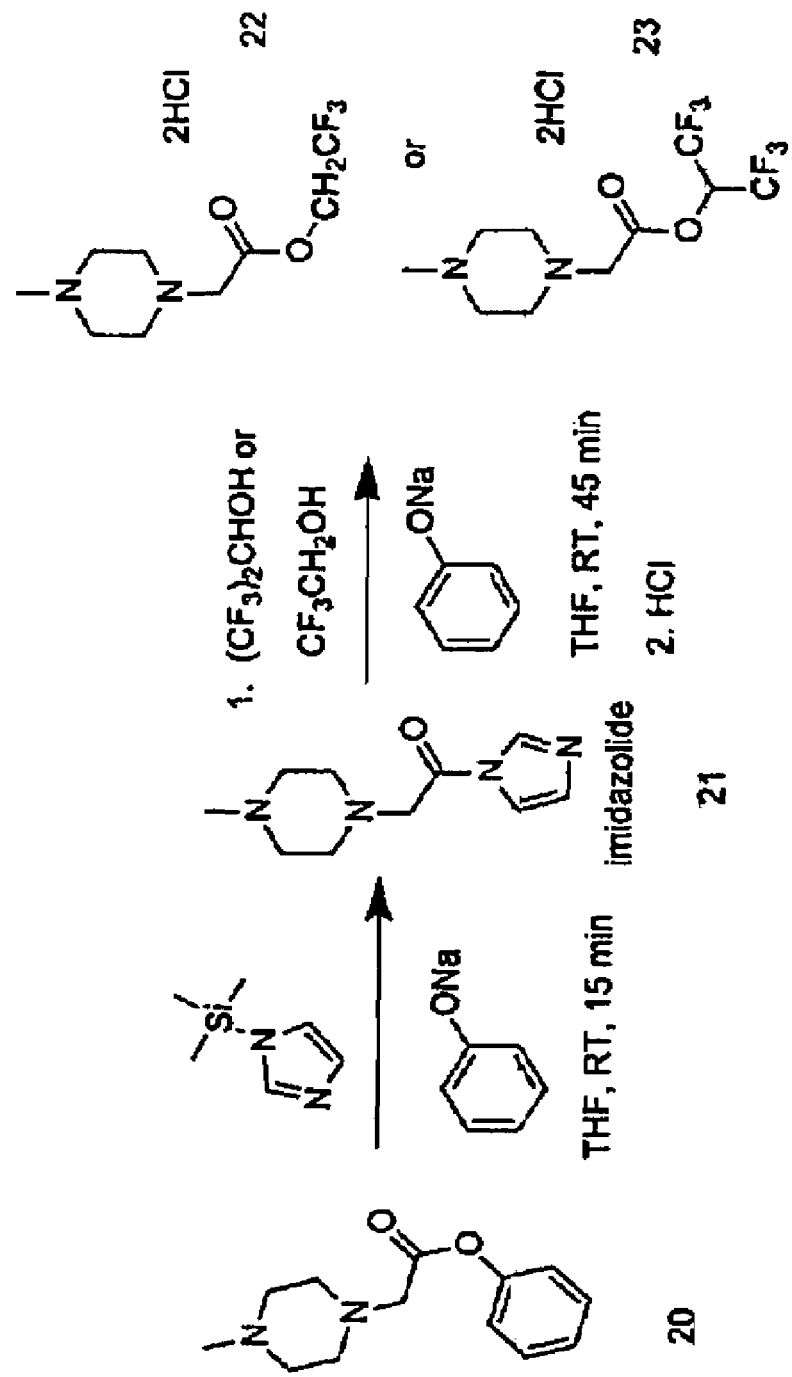
FIG. 4A is an illustration of a synthetic scheme for the synthesis of various active esters of N-methyl piperazine acetic acid.

With reference to FIG. 4A and Example 10, this procedure was used to prepare active esters of 2,2,2-trifluorethanol and 1,1,1,3,3,3-hexafluoro-2-propanol. According to the figure and the example, the phenyl ester of N-methyl piperazine acetic acid (20) was treated with trimethyl silyl imidizole (TMS-imidizole) and sodium phenoxide to form the imidazolide of N-methyl piperazine acetic acid (21). The imidazolide (21) was then reacted with either 2,2,2-trifluorethanol or 1,1,1,3,3,3-hexafluoro-2-propanol to produce the desired active ester of N-methyl piperazine acetic acid (22) or (23), respectively as a bis-acid salt.

In some other embodiments, the active ester can be prepared by conversion of the N-substituted piperazine acetic acid, including isotopically enriched versions thereof, to an acid chloride followed by subsequent reaction of the acid chloride with the alcohol of choice to thereby produce the active ester of the selected alcohol.

Figure 4B:
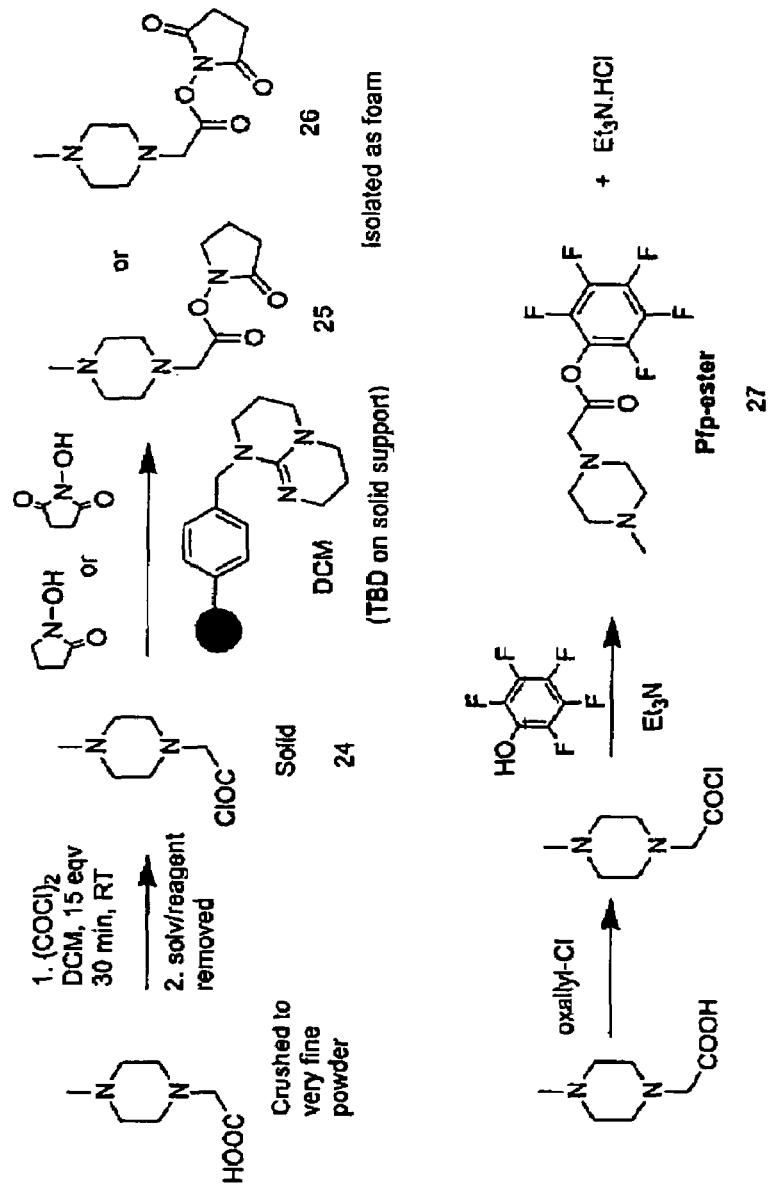
FIG. 4B is an illustration of another synthetic scheme for the synthesis of various active esters of N-methyl piperazine acetic acid.

With reference to FIG. 4B and Example 11, the preparation of the NHS and NHP esters of N-methyl piperazine acetic acid are illustrated using this general procedure. According to the figure and the example, N-methyl piperazine acetic acid is treated with oxalyl chloride to produce the acid chloride (24). The acid chloride is then treated with either of NHP or NHS and solid phase base to thereby produce the active ester (25) or (26), respectively as the free piperazine base (not as an acid salt).

FIG. 4B also illustrates the application of oxalyl chloride to the production of the pentafluorophenyl (Pfp) ester (27) wherein a solution phase base (e.g. triethylamine) is used. The reaction proceeded well with the solution phase base but the hydrochloride salt of the base proved difficult to remove. Application of the solid phase base avoids this caveat.

In still some other embodiments, the active ester can be prepared by treatment of the N-substituted piperazine acetic acid, including isotopically enriched versions thereof, with a trihalooacetate ester of the alcohol that is desired to form the active ester of the N-substituted piperazine acetic acid. In this context, halo refers to fluorine, chlorine, bromine and iodine but preferably to fluorine and chlorine. The trihalooacetate ester has the general formula:

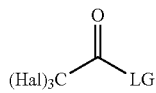

wherein Hal refers to a halogen (fluorine, chlorine, bromine or iodine) and LG refers to the leaving group alcohol. The leaving group (LG) of the trihaloacetate esters can have the following general formula:

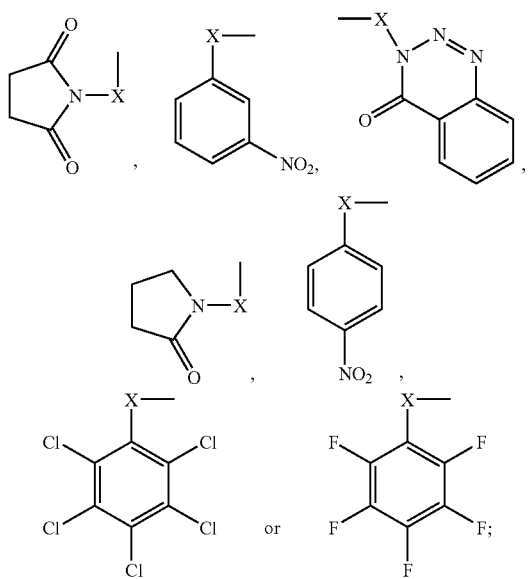

wherein X is O or S, but preferably O. Active esters of N-methyl piperazine acetic acid comprising these leaving groups (LG) were successfully prepared using the identified trifluoroacetate esters (where X is O).

This procedure can be applied to the N-substituted piperazine acetic acids whether they are the acid salt or the zwitterion form. The N-substituted piperazine acetic acids can be reacted with the triholoacetate ester of the alcohol to thereby produce the active ester of the N-substituted piperazine acetic acid. A base that can deprotonate the basic nitrogen atoms of piperazine ring can be added to the reaction as need to induce formation of the product when the starting material is an acid salt of N-substituted piperazine acetic acid. The active ester of the N-substituted piperazine acetic acid can itself be isolated as the mono-acid salt or the di-acid salt. (e.g. the mono-TFA salt, the mono HCl salt, the bis-TFA salt or the bis-HCl salt.). When the trihalooacetate ester is reacted with an N-substituted piperazine acetic acid the product can be:

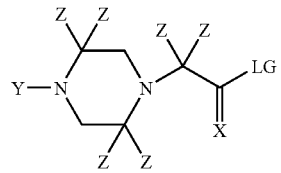

or a salt thereof, wherein X, Y and Z are previously defined. The group LG is the leaving group of the active ester that is displaced by the reactive group of an analyte to be labeled; in essence the leaving group is the alcohol used to form the active ester.

Certain trihaloacetate esters are commercially available. For example, the trifluoracetate esters of pentafluorphenol and 4-nitrophenol can be purchased from commercial sources. However, the others can be obtained by reacting the desired alcohol with trihaloacetic anhydride. With reference to Table 1, below, the trifluoroacetate esters of Pcp, Dhbt, NHS, 3-NP and NHP were prepared by reacting the respective alcohol with trifluoracetic anhydride. The general procedure for such reactions can be found in Example 12. Other alcohols that can be used to produce trihaloacetate esters suitable for the formation of other active esters can also be used.

Figure 4C:
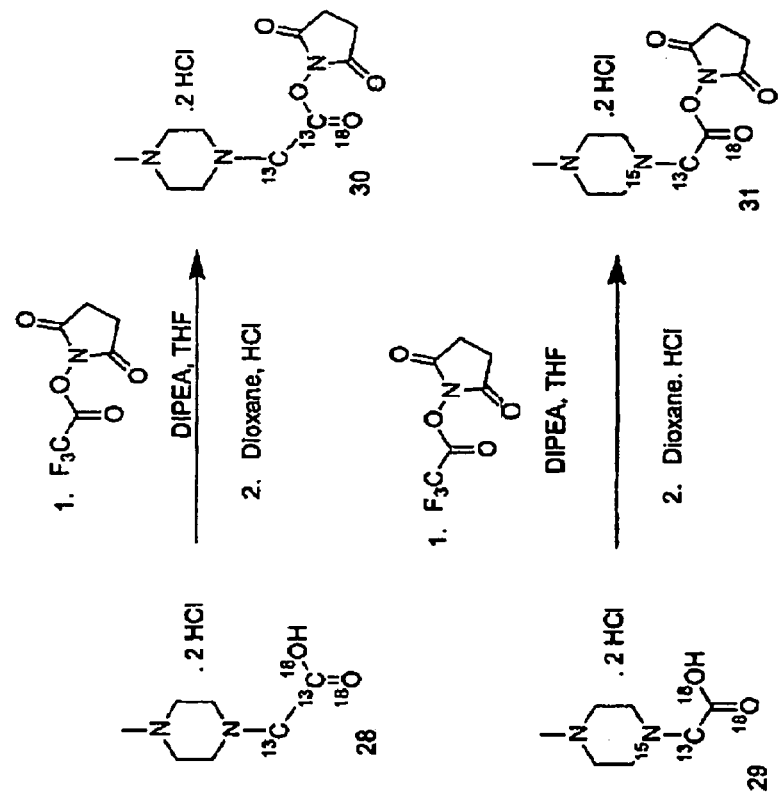
FIG. 4C is an illustration of yet another synthetic scheme for the synthesis of various active esters of N-methyl piperazine acetic acid.

FIG. 4C illustrates the production of the 114 and 115 labeling reagents as the NHS ester. Accordingly, the procedure was successfully applied to the production of isotopically enriched active esters of N-substituted piperazine acetic acids. These active ester reagents were produced as the bis-HCl salts from the bis-HCl salts of the piperazine base.

Figure 4D:
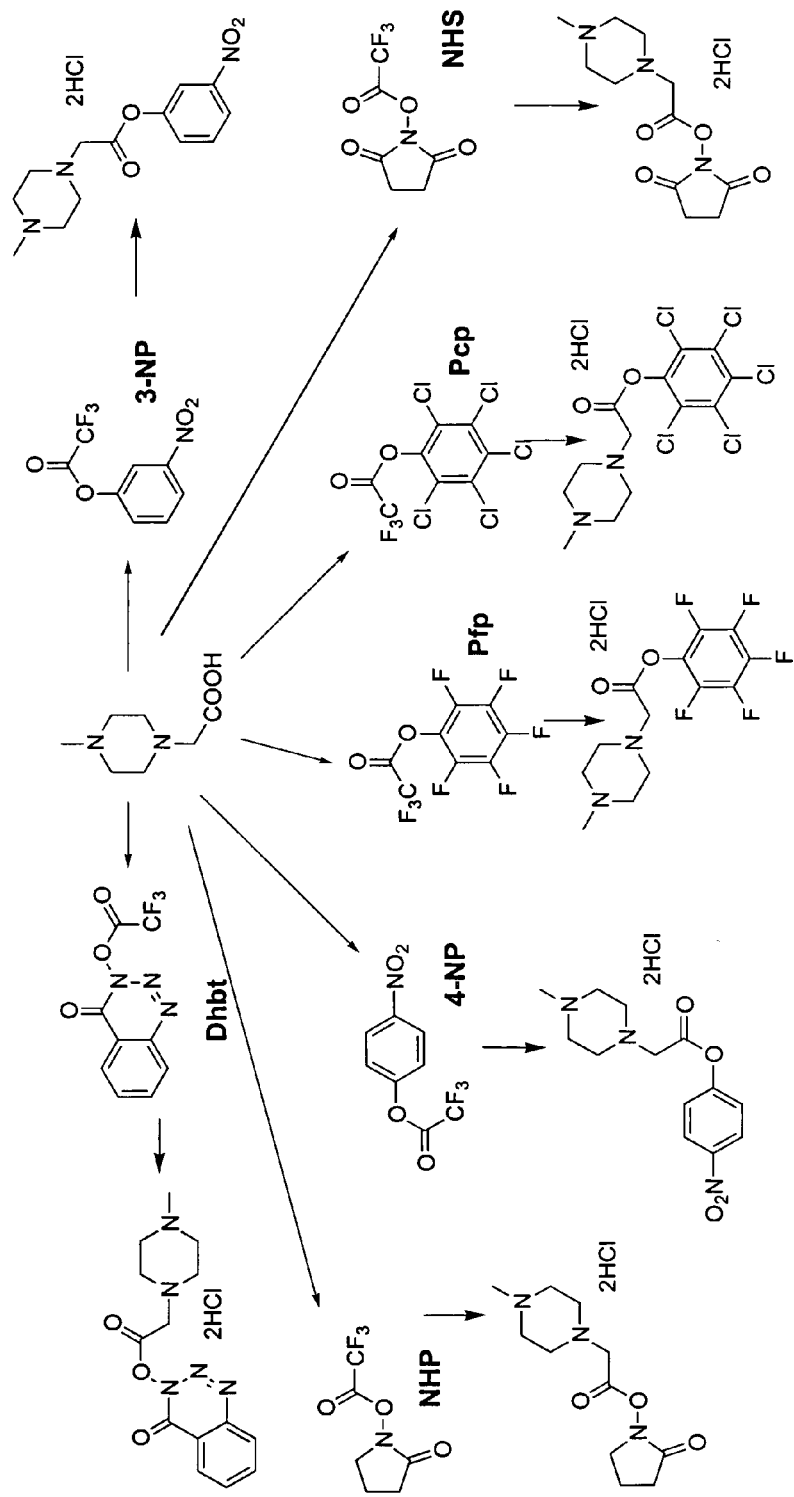
FIG. 4D is an illustration of still another synthetic scheme for the synthesis of various active esters of N-methyl piperazine acetic acid.

FIG. 4D illustrates the production of numerous other active esters of N-methyl piperazine acetic acid that were produced using this generic process. As will be appreciated by the ordinary practitioner, this procedure is generic and robust and can be applied to the production of numerous other active esters of a plethora of N-substituted piperazine acetic acid derivatives.

Figure 5A:
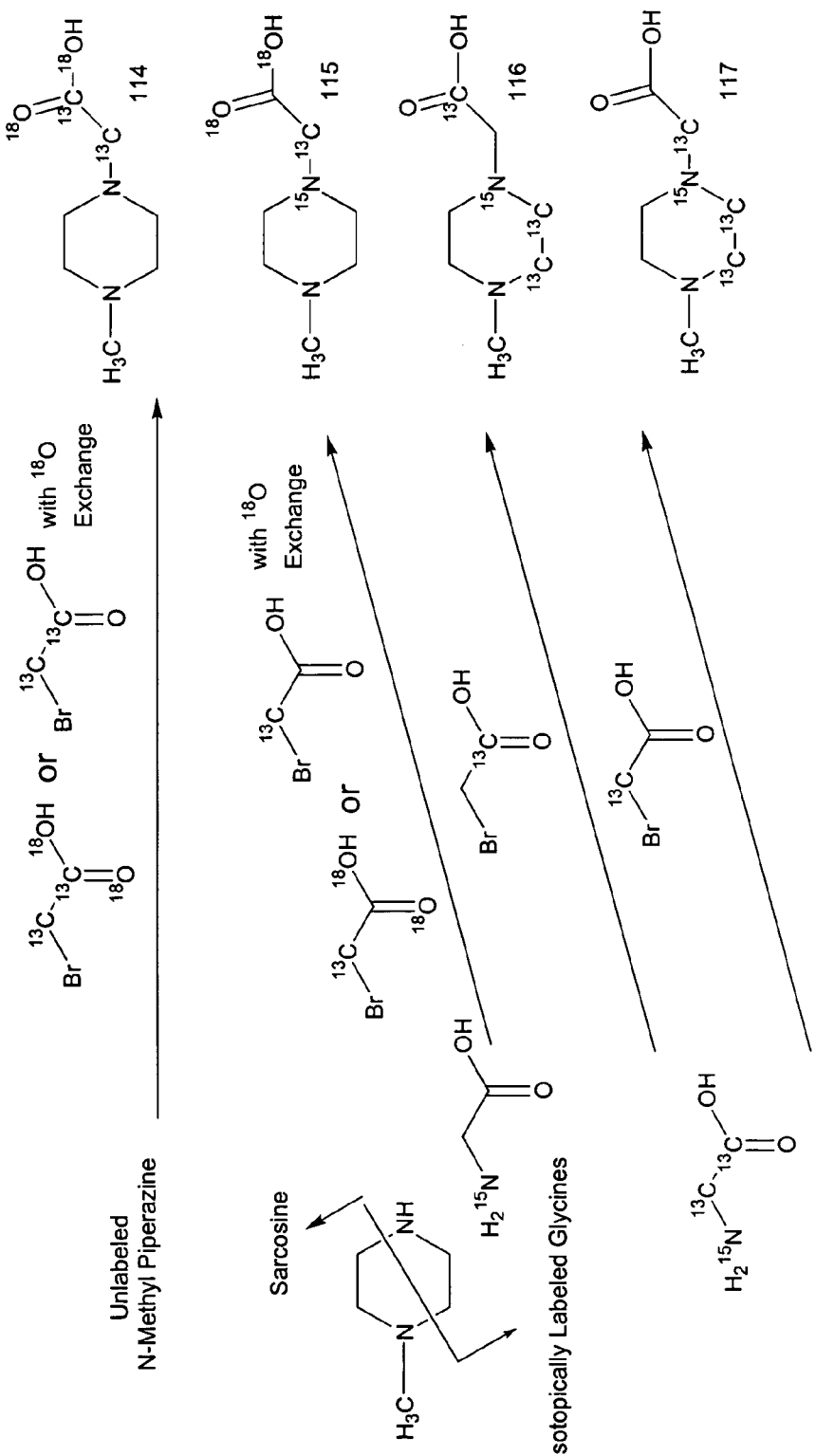
FIG. 5A is an illustration of the heavy atom isotope incorporation pathway for the preparation of four isobaric N-methyl piperazine acetic acids.

V. Isotope Incorporation Pathway for the Preparation of a Set of Isobaric Labeling Reagents FIG. 5A illustrates the general pathway taken to the production of a set of four isobaric labeling reagents identified as 114, 115, 116 and 117. These designations are based upon the "signature ion" each reagent produces upon fragmentation in a mass spectrometer (FIG. 5B). The "signature ion" can be used to deconvolute information associated with different samples in a multiplex assay as discussed in the Introduction.

The pathways illustrated in FIG. 5A utilize the procedures set forth above for the production of N-substituted piperazine acetic acids, and active esters thereof. In particular, suitable isotopically labeled glycines were used in the preparation of suitable isotopically labeled N-substituted piperazines (e.g. N-methyl piperazines). The labeled and unlabeled N-methyl piperazines can be treated with isotopically labeled bromoacetic acid derivatives, with or without subsequent $^{18}$O enrichment to thereby produce the N-methyl piperazine acetic acid compounds of desired structure. These suitably labeled N-methyl piperazine acetic acid compounds were used as labeling reagents; in the present case by conversion to an active ester for coupling with analytes such as peptides.

All four of the labeling reagents (114, 115, 116 and 117) were produced as NHS esters. All four reagents were used to label peptides, including peptides (analytes) obtained from digested protein. The set of reagents (two or more of them), were shown to be suitable for the multiplex analysis, including proteome analysis, as described in copending and co-owned application Ser. No. 60/443,612, incorporated herein by reference.

For example, two or more samples containing digested peptides as the analyte, each sample being labeled with one of the isobaric labeling reagents (114, 115, 116 or 117), were mixed to form a mixture that was analyzed in a tandem mass spectrometer. After the first MS analysis, selected ions, of a particular mass representing a mixture of fragment ions of the same analyte labeled with two or more different isobaric labels, were subjected to dissociative energy causing fragmentation of the selected ions. The selected ions, and the fragments thereof, were then re-analyzed in the mass spectrometer wherein signature ions of the isobaric labeling reagents used to label the analytes, as well as daughter ions of the analyte, were observed.

VI. State of Isotopic Enrichment

The various N-substituted piperazines, N-substituted piperazine acetic acids and active esters of N-substituted piperazine acetic acid can be prepared with starting materials of greater than 80 percent isotopic purity of for each heavy atom isotope. The isotopic purity can be greater than 93 percent for each heavy atom isotope in some starting materials. In other starting materials the isotopic purity can be greater than 96 percent for each heavy atom isotope. In still other starting materials the isotopic purity can be greater than 98 percent for each heavy atom isotope. When performing an $^{16}O$ to $^{18}O$ exchange, it was possible to routinely obtain carboxylic acid groups of 96 or greater percent isotopic purity (per oxygen atom) of the heavy atom isotope.

Because, with the exception of $^{18}O$ which can be exchanged with $^{16}O$ in certain cases, the isotope purity and composition of starting materials will translate directly into the isotopic purity of the products. Moreover, for $^{18}O$, it has been shown that isotopic purity of greater than 96 percent (per atom) can be achieved using the methods described herein. Accordingly, in some embodiments, this invention pertains to N-substituted piperazines, N-substituted piperazine acetic acids and/or active esters of N-substituted piperazine acetic acid having an isotopic purity of at least 80 percent for each heavy atom isotope. In some other embodiments, this invention pertains to N-substituted piperazines, N-substituted piperazine acetic acids and/or active esters of N-substituted piperazine acetic acid having an isotopic purity of at least 93 percent for each heavy atom isotope. In still some other embodiments, this invention pertains to N-substituted piperazines, N-substituted piperazine acetic acids and/or active esters of N-substituted piperazine acetic acid having an isotopic purity of at least 96 percent for each heavy atom isotope. In yet some other embodiments, this invention pertains to N-substituted piperazines, N-substituted piperazine acetic acids and/or active esters of N-substituted piperazine acetic acid having an isotopic purity of at least 98 percent for each heavy atom isotope.

The following examples are illustrative of the disclosed compositions and methods, and are not intended to be limit the scope of the invention. Without departing from the spirit and scope of the invention, various changes and modifications of the invention will be clear to one skilled in the art and can be made to adapt the invention to various uses and conditions. Thus, other embodiments are encompassed.

EXAMPLES

General Synthetic Notes: Unless otherwise stated, chemicals were purchased from commercial sources and used as received. Unless otherwise stated, the following chemicals were purchased from Sigma-Aldrich. Trifluoroacetic anhydride (TFAA, P/N 106232), N-Hydroxysuccinimide (NHS, P/N 13067-2), tert-Butyl bromoacetate (P/N 124230), 4-Nitrophenyl (4-NP) trifluoroacetate (P/N N22657), Pentafluorophenyl (Pfp) trifluoroacetate (P/N 377074), tert-butyldimethylsilyl (TBDMS) cyanide (407852), 1-(Trimethylsilyl) imidazole (P/N 153583), Phenyl bromoacetate (P/N 404276), Pentachlorophenol (Pcp-OH, P/N P2604), 2,2,2-Trifluoroethanol (P/N 326747), 1,1,1,3,3,3-Hexafluoro-2-propanol (HFI-OH, P/N 105228), (3-Hydroxy-1,2,3-benzotriazin-4(3H)-one (Dhbt-OH, P/N 327964), Oxalyl chloride (P/N 320420), 1-Methylpiperazine (P/N 130001), Tetrahydrofuran (THF dry, P/N 186562). Dichloromethane (DCM dry, P/N 270997), 4 M hydrochloric acid (HCl) solution in dioxane (P/N 345547), HCl (gas, P/N, 295426), 3-Nitrophenol (3-NP-OH, P/N 163031) 1,5,7-Triazabicyclo[4.4.0]dec-5-ene (TBD) bound to polystyrene crosslinked with 2% DVB, Capacity (base): ~2.6 mmol/g (ss-TBD, Fluka, P/N 90603), $H_2^{18}O$ (Isotec, 95 $^{18}O$ atom % (P/N 329878) or 99% $^{18}O$ atom % (P/N 487090)), $Br^{13}CH_2COOEt$ (Cambridge Isotope Laboratories (CIL), P/N CLM-1010-5), $Br^{13}CH_2^{13}COOEt$ (CIL, P/N CLM-1011-1), $BrCH_2C^{18}O^{18}OH$ (Isotec, P/N 597031). All moisture sensitive reactions were performed under nitrogen or argon atmosphere.

Isotopically enriched starting materials were generally obtained from either Isotec (a Sigma-Aldrich company) or Cambridge Isotope Laboratories (Andover, Mass.). Generally, the most highly enriched starting materials were obtained and used in the production of the isotopically enriched piperazine derivatives. However, the state of isotopic enrichment of starting materials is a choice which the ordinary practitioner will appreciate strikes a balance between the price of the starting materials (wherein the higher the state of isotopic enrichment, the higher the price) and requirement for purity of the enriched isotopes in the final product. Accordingly, the ordinary practitioner will appreciate that the most practical method of synthesis of isotopically enriched compounds may not always proceed through the most common synthetic routes. Indeed, there may be two or more different routes to the different isotopic variants of the same compound. Thus, for some reactions and/or compounds described herein, various synthetic routes have been undertaken and are therefore discussed below. Certain advantages and caveats pertaining to these routes are also discussed.

I. Synthesis of Isotopically Labeled N-Methyl Piperazines

Note: Unlabeled N-methyl piperazine (a.k.a. 1-methyl piperazine) is commercially available from a variety of sources. However, no source for any type of isotopically enriched N-methyl piperazine (as a stock item) could be found. It was determined however that suitably protected glycine and sarcosine could be condensed, cyclized and the product (a diketone) could be reduced to thereby produce N-methyl piperazine (See FIG. 1). Furthermore, it was determined that all possible permutations of $^{15}N$ and $^{13}C$ isotopically labeled glycine, as well as partially protected versions thereof (e.g. t-boc protected amino acids), were commercially available from sources such as Isotec or Cambridge Isotope Laboratory, Inc. Accordingly, this appeared to be a promising route to various N-methyl piperazine compounds comprising one or more heavy atoms. Because appropriately protected (t-boc) isotopically enriched glycines and suitably protected sarcosine can be purchased from commercial sources and because the protection of amino acids, such as glycine and sarcosine, are well-known, this discussion of the synthetic route to N-methyl piperazine begins with the suitably protected amino acids (FIG. 1).

Example 1

General Procedure for the Condensation of Sarcosine Ester and t-boc-Glycine (FIG. 1)

Note: Sarcosine is commercially available as either the methyl or the ethyl ester. Either can be used in the condensation reaction.

To a round bottom flask (RBF) was added 1.1 equivalent (eq.) of sarcosine ethyl ester (2) and 1 eq. of t-boc-glycine (1) (including isotopically labeled t-boc-glycines for the production of various isotopically labeled N-methyl piperazines). The solid was then dissolved with the addition of dichloromethane (DCM) (~20 mL/g of t-boc-glycine). To this stirring solution was added 1.1 eq. of N-methyl morpholine (NMM) then 1.1 eq. of dicyclohexylcarbodiimide (DCC) in DCM. A precipitate formed within minutes. The reaction was stirred overnight. The reaction was monitored by thin layer chromatography (TLC). If t-boc-glycine was still present, additional DCC in DCM was added. When the reaction was determined to be complete, the solids were filtered off and the cake was rinsed with DCM. The product containing solution was then evaporated to dryness.

The product was purified by silica gel chromatography using a column packed in 50% ethyl acetate (EtOAc)/hexane. A small amount of the 50% EtOAc/hexane solution was used to dissolve/suspend the dried down product (not all will dissolve). This solution/slurry was loaded onto the packed column. The column was eluted 50% EtOAc/hexane to obtain the minimally retained product. Product containing fractions were evaporated to provide an oil, speckled oil, or flaky solid (materials that are higher in heavy atom isotope content appeared to exhibit more characteristics of a solid).

| TLC conditions: EtOAc (developed with ninhydrin and heat) | |
| --- | --- |
| Product (3) | Rf~0.85 |
| t-boc-glycine (1) | Rf~0.3 (broad tailing) |
| Sarcosine-OEt (2) | Baseline |
| NMM | Faintly visible just above sarcosine |

Example 2

General Procedure for the Synthesis of 1-Methyl-2,5-Diketopiperazine (FIG. 1)

A solution of 1:1 trifluoroactetic acid (TFA):DCM containing 0.5% water was prepared. This solution was added to the column purified product (3) of the condensation reaction (~10 mL/g starting material). The resulting solution was stirred for 30 minutes and then the solvents removed by rotoevaporator. Ethanol (~10 mL/g starting material) was then added to the reaction flask and this solution was again striped to dryness. The procedure was repeated with toluene. The product was again dissolved in ethanol in the reaction flask and anhydrous potassium carbonate (4 eq) was added. The solution bubbled vigorously for a short period following the addition of the potassium carbonate. A drop of the reaction mixture was removed, diluted with water, and the pH of the solution was determined. If the pH was below 8, more potassium carbonate was added. Once the pH was confirmed to be greater than 8, the reaction was allowed to reflux overnight. The warm reaction mixture was then passed through a plug of Celite to remove the excess salts. The cake was rinsed twice with anhydrous ethanol. The filtrate was transferred to a larger flask and stripped to dryness. The product foam was redissolved in 9:1 ethyl acetate-methanol and passed through a plug of silica-gel. The silica-gel was then washed with ~4 column volumes of 9:1 ethyl acetate-methanol. All fractions were evaporated to dryness.

Notes and alternative procedures: Deprotection of the t-boc group with the TFA/DCM/$H_2O$ solution can be followed by TLC (ninhydrin/heat shows conversion of the spot at Rf 0.85 to a dark red-brown spot at origin). After deprotection, it is also acceptable to add methanol, concentrate and re-treat with methanol followed by a second concentration and drying in vacuo to remove excess TFA.

In some reactions, concentrated ammonium hydroxide (large excess ~60 mL per 16 mmol of starting material) was substituted for potassium carbonate. (When concentrated ammonium hydroxide was added to the reaction at room temperature, it generated a white insoluble material and a slightly milky reaction mixture.) After the addition of concentrated ammonium hydroxide, the flask was sealed with septum to prevent loss of ammonia. Cyclization appeared to be complete after overnight (12 hrs) reaction although in some cases heating to 60° C. over several hours was sufficient. The reaction was monitored by TLC (10% MeOH/DCM visualized with 10% phosphomolybdic acid (PMA) in MeOH with heat). The product appeared as a blue spot at Rf 0.54. Since the deblocked material (red-brown spot at origin) could not be visualized with PMA, another TLC was performed as a cross-reference using ninhydrin/heat.

When cyclization was deemed complete by TLC analysis, the mixture was filtered and the flask and solids were rinsed with DCM. The filtrate was concentrated and redissolved in 10% MeOH/DCM before chromatography. The white waxy solids were partially insoluble in the 10% MeOH/DCM so the material was sonicated. Sonification successfully dissolved the mixture that was then applied to the column. The first fraction eluted was mainly the white waxy solid. The major fraction (the dione product (4)) eluted next and was followed by another minor impurity (Rf 0.3). It was observed that in cases where incomplete TFA removal resulted in formation of ammonium triflate, this impurity co-eluted with the product and the secondary material. A second column could be used to completely purify the desired product.

The melting points of the dione (4): 116, 117: 138-139 for model compound: lit: 136-139 (J. Het. Chem 18, 423, 1981); 142-143 (J. Biol. Chem 61, 445, 1924).

TLC condition: 9:1 ethyl acetate-methanol (develop with phosphomolybdic acid and heat)

Product Rf~0.2

Alternative TLC condition: 10% MeOH/DCM; develop with heat

Product (blue spot) Rf=0.54
1H-NMR data

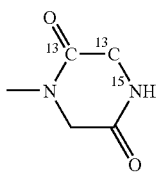

NMR (D$_6$ DMSO)-N1-CH$_3$, d 2.79, 2.80 3H; 3-CH$_2$ dd 3.94, 3.92, 3.59, 3.57 2H; 6-CH$_2$ d 3.87, 3.86 2H; 4-NH b 8.11H.

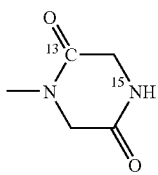

NMR (D$_2$O)-N1-CH$_3$, d 3.00, 2.99 3H; 3-CH$_2$ d 4.08, 4.08 2H, 6-CH$_2$ d 4.14, 4.14 2H.

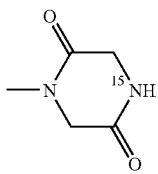

NMR (D$_6$ DMSO)-N-1-CH$_3$, s 2.80 3H; 3-CH$_2$ s 3.76 2H; 6-CH$_2$ s 3.86 2H; 4-NH d 8.03, 8.26 1H.

Example 3

General Procedure for the Synthesis of N-Methyl Piperazine (Route A; FIG. 1)

A saturated solution of sodium sulfate was prepared. Tetrahydrofuran (THF) (4 mL per mmol starting material based upon the material used in Example 2) was added to the diketopiperazine formed using the procedure of Example 2. The reaction flask was fit with a reflux condenser and three equivalents of 1M LiAlH$_4$ in THF (LAH solution; it may be possible to substitute Red-Al or other reducing reagent for LAH but this has not been attempted) was added to the solution through a dropping funnel. There was vigorous hydrogen evolution at the initiation of the addition but this subsided as the addition continued. The reaction was heated to reflux for 4 hours. After the reaction was complete, the solution was cooled to room temperature and the remaining LAH was quenched with the very slow addition of saturated aqueous sodium sulfate (¼ the volume of the LAH solution added). The reaction appeared as a gray suspension.

DCM was added to this suspension (½ volume of the THF) and the gray gel-like solid was removed by filtration. The flask and filtered solids were then thoroughly washed 2× with DCM (¼ volume of the THF). The combined organic solution (DCM/THF) was then dried with Na$_2$SO$_4$ (solid—anhydrous) and filtered. (In some early experiments the N-methyl piperazine was isolated as an oil (free base and not as a TFA or HCl salt) but the product was determined to be a volatile oil and therefore not be isolated in high yield).

Di-tert-butyl-dicarbonate (3 equivalents) was added to this solution that was stirred and vented overnight. TLC was used to monitor the reaction. Once complete, the solvent was removed by rotary evaporation to yield a liquid. This liquid is slightly volatile, so low vacuum evaporation of solvent is recommended (high vacuum conditions should be avoided). The product was dissolved in DCM and loaded onto a silica-gel column packed with 8% methanol in ethyl acetate. Product was eluted with the 8% methanol in ethyl acetate solution. Product containing fractions were determined by TLC, pooled, and evaporated to a liquid. This liquid was taken directly to the deprotection reaction. Note: the t-boc deprotection was performed only as a means to isolate the crude N-methyl piperazine product but this requires subsequent deprotection.

TLC—N-methyl piperazine (develop with ninhydrin)
4:1:1 Ethanol:Water:Ammonium hydroxide
Product Rf=0.6
TLC—N$^1$-t-Boc-N$^2$-methyl piperazine (develop with ninhydrin)
4:1 DCM-MeOH
Product Rf=0.5

Deprotection:

A solution of 1:1 TFA, DCM with 0.5% water was prepared. This solution was added to the material isolated from the reduction, above (~10 mL/g starting material). The reaction was stirred for 30 minutes then the solvent was removed with a rotoevaporator. Solvent evaporation was terminated when no more solvent was observed to be collecting on the condenser. TFA was added to the product residue (~2 mL/g starting material) to form a free flowing solution. The TFA solution was transferred to a centrifuge tube and diethyl ether was added to precipitate the product salt. The solution was mixed using a vortex. The solution was then centrifuged and the supernatant decanted to collect the precipitate. The filtrate was then washed 1 time with ether by resuspending the product, vortexing, and re-centrifugation. Product was dried under low vacuum to remove residual ether.

1H-NMR data:

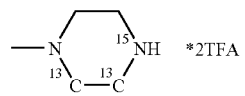

NMR (D$_2$O)-N1-CH$_3$, d 3.02, 3.03 3H; methylenes, broad triplet 3.3-3.9 8H

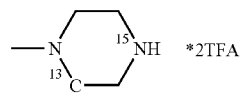

NMR (D$_2$O)-N1-CH$_3$, d 3.02, 3.03 3H; methylenes, broad 3.40-3.85 8H

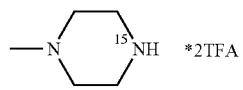

NMR (D$_2$O)-N1-CH$_3$, s 3.03 3H; methylenes, broad 3.50-3.75 8H

Example 4

General Procedure for the Synthesis of N-Methyl Piperazine (Route B; FIG. 1)

The product of the procedure of Example 2 was dissolved in anhydrous THF (5 mL per mmol SM) in a multi-neck RBF fitted with condenser, addition funnel and argon (Ar) inlet. To this solution was added 3 equivalent of the LAH solution slowly through a dropping funnel at RT under Ar. Vigorous hydrogen evolution was observed at the beginning. After addition, the cloudy solution was heated to reflux for 3 hours. TLC was used to determine when the reaction was complete (disappearance of starting material (SM), 10% MeOH/DCM TLC developing solvent, PMA as visualizer). After the reaction was complete, the solution was cooled to room temperature and quenched with the very slow addition of saturated aqueous sodium sulfate (¼ the volume of the LAH solution added). White gel-like solid solution was passed through a plug of Na$_2$SO$_4$ solid to remove H$_2$O. The filter cake was washed with THF several times (400 mL per gram SM) until TLC of the washing showed a little product. Then TFA (4 eq) was added to the THF solution (HCl in dioxane could also be added if the HCl salt was desired). The color of the solution changed to light brown from pale yellow. The solution was concentrated on a rotoevaporator under reduced pressure to yield brown oil. The light brown product was precipitated as bis-TFA salt by adding ether (42 mL per 1 gram SM) to yield of 80% N-methyl-piperazine. $^1$H NMR (D$_2$O) was used to confirm the desired product.

II. Alkylation of N-Methyl Piperazines to Form N-Methyl Piperazine Acetic Acids

Note: FIG. 5A illustrates the pathway for the synthetic incorporation of heavy atom isotopes into four isobaric labeling reagents referred to herein as 114, 115, 116 and 117. As can be seen from FIG. 5A, certain of the heavy atom isotopes can be incorporated by the choice of the commercially available isotopically labeled glycine used in the production of the N-methyl piperazine. Certain other heavy atoms can be incorporated during the alkylation reaction based upon the choice of the commercially available bromoacetic acid. In some cases, the $^{18}$O can be incorporated through an efficient exchange using $^{18}$O labeled water. The labeling reagents are designated 114, 115, 116 and 117 based upon the mass of the fragment that forms a signature ion in the mass spectrometer (see: FIG. 5A and FIG. 5B) once the reagent has been fragmented by the application of dissociative energy.

Figure 2C:
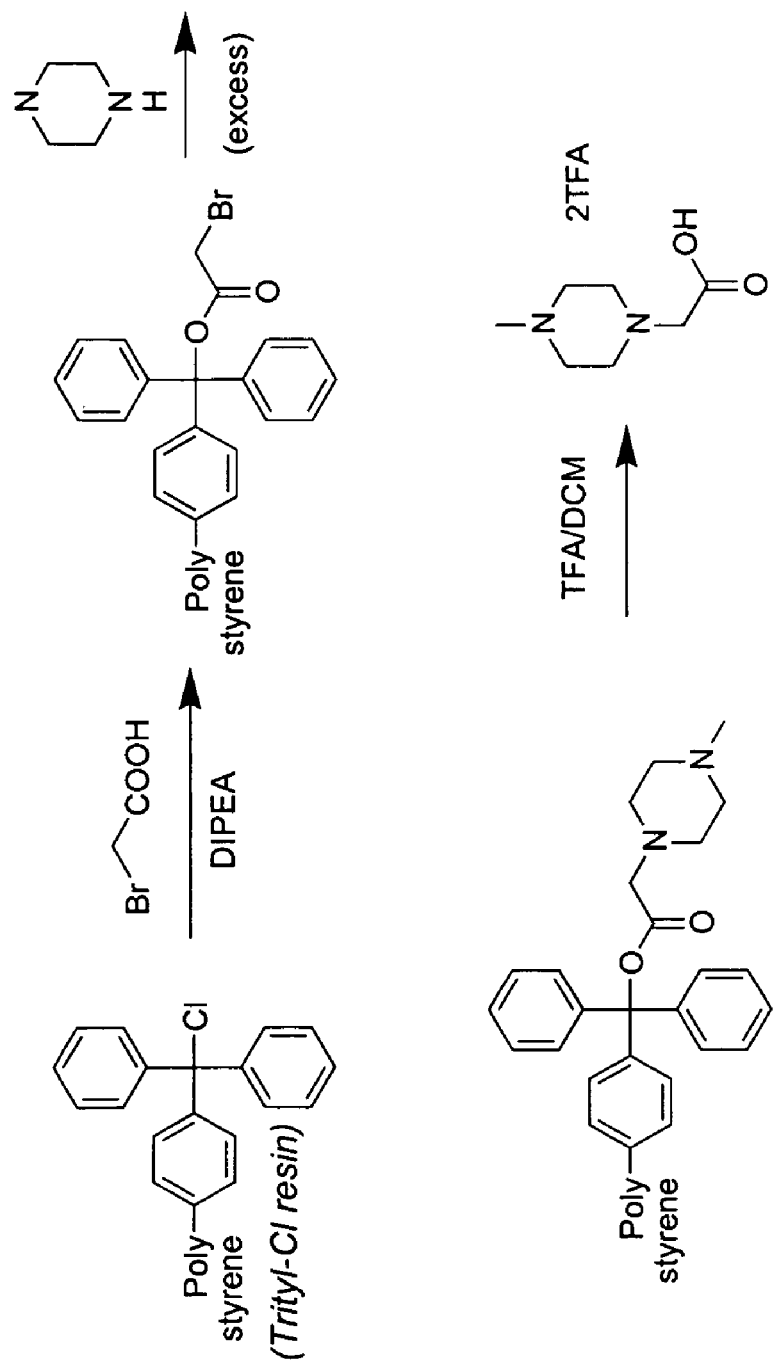
FIG. 2C is an illustration of yet another synthetic scheme for the synthesis of N-methyl piperazine acetic acids.

With reference to FIG. 2A, scheme A is useful for producing the N-methyl piperazine acetic acid as a zwitterion and not as a salt (e.g. mono or bis TFA or HCl salt). With reference to FIG. 2B, scheme B is useful since it requires the use of only one equivalent of N-methyl piperazine for the production of the N-methyl piperazine acetic acid thereby foreclosing the waste of the valuable isotopically labeled starting material. With reference to FIG. 2C, scheme C is useful for alkylations involving the isotopically labeled bromoacetic acid, particularly the $^{18}$O labeled bromoacetic acid as it was expected to reduce the occurrence of $^{18}$O scrambling (or exchange with $^{16}$O from residual water).

Example 5

Procedure for the Synthesis of Isotopically Labeled N-Methyl Piperazine Acetic Acids (Scheme A; FIG. 2A)

To a stirring solution of 1.18 g (11.83 mmol) N-methyl piperazine in 15 mL of toluene at room temperature was added 1 g (5.91 mmol) of ethylbromoacetate, 1,2-$^{13}$C dropwise, over a period of 15 minutes. Immediate formation of white solid was observed. The reaction mixture was then heated in an oil bath at 90° C. for 4 hr. After cooling the mixture to room temperature, the off-white solid was removed by filtration, and washed with 25 mL of toluene. The combined filtrate and washings was then concentrated in a rotoevaporator, and the residue was dried under high vacuum for 5 hours to yield 1.10 g (quantitative) of ethyl ester of N-methyl piperazine acetic acid-1,2-$^{13}$C (9) as an off-white oil. The crude product (9) was analyzed by MS and $^1$H-NMR, and was directly used for the next step without further purification. MS (ESI, m/z): 189.16 (M+1), $^1$H-NMR (DMSOd$_6$) δ 4.2 (m, 2H), 3.4 (d,1H, J=7 Hz), 3.05 (d, 1H, J=7 Hz)), 2.4-2.7 (b, 8H), 2.3 (s, 3H), 1.25 (t, 3H).

A solution of ethyl ester of N-methyl piperazine acetic acid (9) (1.1 g, mmol), prepared as described above, in water (20 mL) was refluxed for 24 hr. The reaction was monitored by MS analysis. After 24 hr, the reaction mixture was concentrated in a rotoevaporator to afford white solid product, which was triturarted with acetone (10 mL) overnight. The product was then separated by filtration and dried under high vacuum overnight at 45° C. in a vacuum oven, to yield 780 mg of N-methyl piperazine acetic acid, 1,2-$^{13}$C (10), as a white powdery solid. 300 mg of the product was further purified by sublimation (1 mm/Hg, 110-120° C.) to yield 270 mg of white solid. MS (ESI, m/z); 161 (M+1), $^1$H-NMR (DMSOd$_6$) δ 3.3 (d, 1H, J=7 Hz), 2.95J=7 Hz), 2.55-2.75 (b, 4H), 2.3-2.45 (b, 4H), 2.18 (s, 3H)

Notes: This procedure utilizes unlabeled N-methyl piperazine. This procedure is useful for producing the zwitterion of N-methyl piperazine acetic acid.

The product can also be isolated as the mono or bis-HCl or mono or bis-TFA salt by treatment with the appropriate acid prior to or subsequent to its isolation as described above.

Example 6

Procedure for the Synthesis of Isotopically Labeled N-Methyl Piperazine Acetic Acids (Scheme B; FIG. 2B)

To a slurry of 200 mg (1.14 mmol) of N-methylpiperazine-$^{15}$N 2HCl (the 2TFA salt can also be used) in methanol (MeOH, 14 mL), was added 1.76 g (4.59 mmol) of ss-TBD, with a loading of 2.6 mmol/g, followed by CH$_2$Cl$_2$ (6 mL). The mixture was then sonicated for 15 minutes and was then cooled in an ice bath under an argon atmosphere. To this vigorously stirred slurry, a solution of 193 mg (1.14 mmol) of ethylbromoacetate-2-$^{13}$C in acetonitrile (3 mL) was added dropwise using a syringe pump (maintaining a rate of 2 mL/hr). After completion of the addition, the ice bath was removed and the mixture was continued stirring at room temperature overnight (18 hr). The mixture was then filtered through a sintered funnel, and the solid was washed several times with MeOH (4×10 mL). The combined filtrate and washings were then concentrated in a rotoevaporator, and the residue was kept under high vacuum to yield 111 mg (51%) of the ethyl ester of the N-methyl piperazine acetic acid (11) as an off white solid. This crude product was directly used for the next step without further purification. MS (ESI, m/z) 189 (M+1). $^1$H-NMR (DMSOd$_6$) δ 4.05 (q, 2H), 3.3 (s, 1H), 3.0 (s, 1H), 2.4-2.5 (b, 4H), 2.2-2.4 (b, 4H), 2.1 (s, 3H), 1.15 (t, 3H).

The product was hydrolyzed in the manner described in Scheme A, above. The following analytical data was obtained for the product.

MS (ESI, m/z) 161 (M+1). $^1$H-NMR (DMSOd$_6$) δ 3.35 (s, 1H), 3.05 (s, 1H), 2.65-2.8(b, 4H), 2.5-2.65(b, 4H), 2.35 (s, 3H),

Without substantial variation, above general procedure was applied to other isotopically labeled N-methyl piperazines to produce various isotopically labeled N-methyl piperazine acetic acid derivatives.

The product can also be isolated as the bis-HCl or bis-TFA salt by treatment with the appropriate acid prior to or subsequent to its isolation as described above.

Example 7

General Procedure for the Synthesis of Isotopically Labeled N-Methyl Piperazine Acetic Acids (Scheme C; FIG. 2C)

To a solution of bromoacetic acid (715 mg, 5 mmol) in DCM (15 mL) was added 700 mg of trityl-Cl resin (1 mmol, 1.45 mmol/g) followed by diisopropylethylamine (DIPEA) (1.79 mL, 10 mmol). This solution was mixed at room temperature for 1 hour. The resin was then filtered and washed with dichloromethane (3×4 mL) followed by a wash with a solution of dichloromethane-methanol-DIPEA (17:2:3, 5 mL) and finally a wash with dichloromethane (3×4 mL).

The resin was then treated with a solution of N-methyl piperazine (N-MP) (0.57 mL, 5 mmol) in DMF (5 mL) for 30 minutes and then washed with DMF and dichloromethane (3×4 mL each). The N-MPA so generated on resin was cleaved with a 25% solution of TFA in dichloromethane (10 mL for 5 min)) and resin was washed with the same solution (2×5 mL). After evaporation of TFA, the product was precipitated and washed with ether (388 mg, 99% yield, bis TFA salt). The product was identified by NMR (matched with literature) and with ES-MS (Calculated MH$^+$=159.11, found 159.14).

Without substantial variation, the above general procedure was applied to other isotopically labeled N-methyl piperazines to produce various isotopically labeled N-methyl piperazine acetic acid derivatives.

The product could also be isolated as its bis-HCl salt if HCl was used to cleave the product from the support rather than TFA. Other acids could also be used for the cleavage reaction and product would be the salt of the acid used.

III. Methods for the Incorporation of $^{18}$O into N-Methyl Piperazine Acetic Acids Note: In the initial experiments, incorporation of $^{18}$O into the N-methyl piperazine acetic acid was attempted as illustrated in FIG. 3A using $^{18}$O labeled bromoacetic acid (custom synthesized by CIL). Caveats to this approach include the possibility that in subsequent reactions, the $^{18}$O can exchange with $^{16}$O from residual water or can otherwise exchange with $^{16}$O from other reagents during the esterification process. The more recently applied synthetic procedure is illustrated in FIG. 3B and capitalizes on the $^{16}$O $\Leftrightarrow$ $^{18}$O exchange reaction, using H$_2$$^{18}$O to drive the equilibrium reaction to formation of the desired heavy version of the N-methyl piperazine acetic acid. Though both schemes have been shown to work, Scheme B currently supports the production of the most highly $^{18}$O enriched products.

Example 8

General Procedure for the Synthesis of $^{18}$O Isotopically Labeled N-Methyl Piperazine Acetic Acids, Including Conversion to the Active Ester (Scheme A; FIG. 3A)

To a solution of TBDMS-CN (172 mg, 1.190 mmol)) in DCM (0.575 mL) was added $^{18}$O labeled bromoacetic acid (13) (170 mg, 1.189 mmol) under an argon atmosphere and the solution was heated to 80° C. for 20 minutes and then cooled to room temperature. The product (14) was isolated as an oil (254 mg, 85% yield). $^1$H NMR (CDCl$_3$) δ 3.58 (2H, —CH$_2$—), 0.955 (9H, (CH$_3$)$_3$—Si), 0.30 (6H, CH$_3$Si).

A solution of BrCH$_2$C$^{18}$O$_2$-TBDMS (14) (254 mg, 1 mmol) in DCM (2.5 mL) was added (34 μL/min) to an argon flushed flask containing N-MP (110 μL, 1 mmol), TBD resin (576 mg, 1.5 mmol, 2.6 mmol/g) and DCM at 0° C. After the addition was complete the reaction continued for 1 h at RT and then the resin was filtered and washed with DCM. Combined filtrate was concentrated by rotary evaporation to obtain 118 mg (42% yield) of an oil (15).

Note: Because of the potential for $^{18}$O⇔$^{16}$O exchange during the esterification, the N-methyl piperazine acetic acid prepared by this route was not converted to the active ester using the trifluoracetate procedure described in Section VI, below. Instead it was converted using oxalyl chloride and NHS as described below.

To a solution of $^{18}$O containing TBDMS ester of N-MPA (15) as obtained above (118 mg, 0.427 mmol) in DCM (5 mL) was added a solution of oxalyl chloride (0.427 mL, 0.854 mmol, 2 M solution in dichloromethane) at room temperature. The reaction allowed to continued for 1 hour when an off white slurry formed. Solvent and excess reagent were removed from the reaction mixture. A solution of NHS (50 mg, 0.427 mmol) in dry THF (1.4 mL) was added to the resulting solid followed by 5 mL of dichloromethane, 4 mL of THF and 246 mg of ss-TBD resin (0.640 mmol, 2.6 mmol/g). The mixture was sonicated and mixed for 20 minutes, after which the resin was filtered and washed with 5 mL of dry dichloromethane. To the filtrate so obtained was added 2 mL of 4.0 M solution of HCl in dioxane and the precipitate (16) was washed with dry THF (5 mL×2) and hexanes (5 mL) and dried under vacuum (10 mg, 7% yield). ES-MS (direct infusion in i-propanol) shows isotopic purity to be around 74% at this stage.

Example 9

General Procedure for the Synthesis of $^{18}$O Isotopically Labeled N-Methyl Piperazine Acetic Acids (Scheme B; FIG. 3B)

200 mg (1.24 mmol) of N-methyl piperazine acetic acid 1,2-$^{13}$C (17) was weighed out in a 5 mL plastic vial flushed with argon. The vial was then transferred into a glove box and 2.5 mL of $^{18}$O-water (>99% $^{18}$O) was added. The vial was then fitted with a silicone septum, and a low stream of HCl gas was then passed through the solution using a long needle after venting the septum with an open needle. When the solution had warmed (~2 min), the HCl passage was stopped, and the septum was replaced with a screw-cap. The vial was then heated at 80° C. in a heating block for 18 hr. An aliquot was analyzed by MS and $^{18}$O purity was calculated as 93%. The reaction mixture was then concentrated to dryness in a speedvac, and the residue was subjected to a second cycle of $^{18}$O-exchange as described above. By MS analysis the $^{18}$O purity after the second cycle was determined as 96%. The mixture was then evaporated to dryness in a speedvac, and traces of water were removed by co-evaporataion with toluene (1 mL×2). 220 mg of N-methyl piperazine acetic acid-1,2-$^{13}$C-$^{18}$O$_2$.2HCl (18) was obtained. MS (ESI, m/z), 165 (M+1)

Note: The product was used without further purification in the production of active ester of the N-methyl piperazine acetic acid. The bis-TFA salt was also produced using the above-described procedure wherein TFA was substituted for HCl.

IV. Preparation of the Active Esters of the N-Methyl Piperazine Acetic Acids

Note: Several methods were employed for the production of active esters of N-methyl piperazine acetic acid. The procedure illustrated by Scheme A (FIG. 4A) worked well for the production of the fluoroalcohol esters of N-methyl piperazine (See: FIGS. 4C and 4D). The procedure illustrated by Scheme B (FIG. 4B) produced various active esters of N-methyl piperazine but unless the solid phase base was used (e.g. ss-TBD), the hydrochloride salt of solution phase base was difficult to remove. The procedure illustrated by Scheme C (FIGS. 4C and 4D) proved to be the most generally applicable route to the production of active esters of N-methyl piperazine.

Example 10

Synthesis of Active Esters of N-methyl Piperazine Acetic Acid Via Imidazolide Formation (Scheme A, FIG. 4A)

To a solution of N-methyl piperazine phenyl ester (20) (100 mg, 0.426 mmol) and sodium phenoxide (1 mg, 9 μmol) in THF (5 mL) was added TMS-imidazole (69 μL, 0.468 mmol). The solution was mixed for 20 minutes to generate the imidazolide (21). CF$_3$CH$_2$OH (80 μL, 0.213 mmol) was then added to the light yellow solution so obtained. The solution was mixed for another 30 minutes when TLC indicated clean formation of product (R$_f$=0.6, 4:1 DCM-MeOH). The reaction was then diluted to 15 mL with EtOAc and the product (22) was precipitated by addition of HCl solution in dioxane (4 M, 2 mL). After washing with THF (2×15 mL) product was isolated as white solid. NMR of the solid indicated a 1:1 mixture of product and imidazole (as HCl salt). Calculated MH$^+$=241.13, found=241.12.

1,1,1,3,3,3-Hexafluoro-2-propanol ester (23) was isolated using the general procedure set forth above provided however that (CF$_3$)$_2$CHOH was substituted for CF$_3$CH$_2$OH. The following analytical data was obtained for this product. (R$_f$=0.37, 9:1 DCM-MeOH). Calculated MH$^+$=309.11, found=309.11.

Note: N-methyl piperazine phenyl ester was prepared by the alkylation procedures described above (See FIGS. 2A and 2B) wherein phenyl bromoacetate is substituted for ethyl bromoacetate.

Example 11

Synthesis of Active Esters of N-Methyl Piperazine Acetic Acid Via Oxalyl Chloride (Scheme B, FIG. 4B)

To a suspension of N-methyl piperazine acetic acid (N-MPAA) (79 mg, 0.5 mmol) in DCM (25 mL) was added a solution of oxalyl chloride (4 mL, 0.8 mmol, 2.0 M solution in DCM) over 10 minute at room temperature. After another 30 minutes of reaction, solvent and excess reagent were removed under reduced pressure to give a white solid (24). A solution of NHS (57 mg, 0.5 mmol) in DCM (25 mL) was added to the solid followed by ss-TBD (390 mg, 1 mmol, 2.6 mmol/g). The resulting solution was sonicated for 5 minute when all solid dissolved. The ss-TBD resin was removed by filtration and solvent was evaporated to yield a white foam (97% yield). Product was characterized by ES-MS as before.

Synthesis of Active Esters of N-Methyl Piperazine Acetic Acid Via Trifluoroacetate Esters (Scheme C, FIGS. 4C and 4D)

Note: Conversion of the N-methyl piperazine acetic acids (N-MPAAs) to their active esters via the trifluoracetate ester is typically a two-step process. Except for the rare case where the reagent is commercially available (See: Table 1), the first step involves the preparation of a reagent for esterifying the acetic acid. The second step involves reacting the esterifying reagent with the N-methyl piperazine acetic acid to produce the active ester. Various active esters were produced and tested for the aqueous labeling of peptides. Though the NHS ester proved to be quite useful for this application, other esters may prove useful in other applications. Nevertheless, this method of producing the active esters proved to be quite robust and generally applicable across a wide variety of compounds. FIG. 4B illustrates 7 different active esters that were produced using the same generic procedure.

Example 12

Synthesis of N-Hydroxysuccinimide Trifluoroacetate[10,11] and Other Trifluoroacetate Esters Trifluoroacetic anhydride (4.9 mL, 4×8.68 mmol (2.5-4 equivalents is typically used) was added to N-hydroxysuccinimide (NHS) (1 g, 8.69 mmol) and stirred under argon for 1-2 h to produce a homogeneous reaction mixture. Excess reagent and by-product CF$_3$COOH were removed under reduced pressure (rotary evaporation). The product was obtained as white solid in quantitative yield. The solid was dried under high vacuum for 3-4 h and stored under argon (Ar) or nitrogen (N$_2$) gas.

With reference to FIG. 4D and Table 1, the trifluoroacetate ester of pentafluorophenol (Pfp) and 4-nitrophenol (4-NP) were commercially available. The remaining trifluoroacetate esters were synthesized using the above-described generic procedure provided however that the reaction time and temperature were varied. Furthermore, in some cases the products were isolated by distillation. Yields of the trifluoroacetate esters were good and in some cases near quantitative. The specific conditions used are set forth in Table 1, below.

TABLE 1

| pKa | | |
|---|---|---|
| 4.68 | 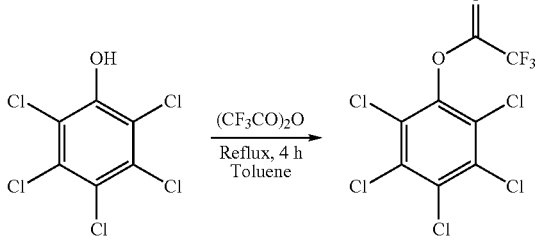 | Pcp |
| 5.50 | 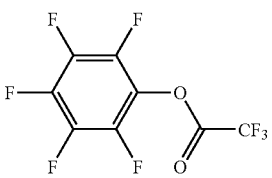 | Pfp |
| 7.23 | 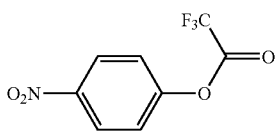 | 4-NP |
| 7.78 | 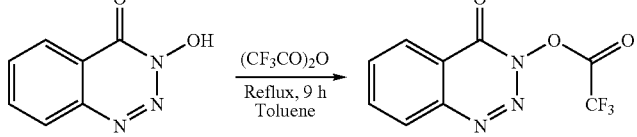 | Dhbt |
| 7.80 | 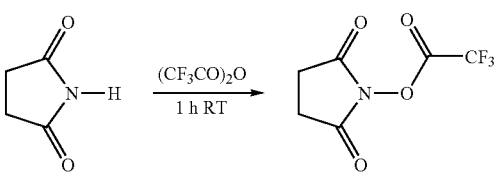 | NHS |
| 8.33 | 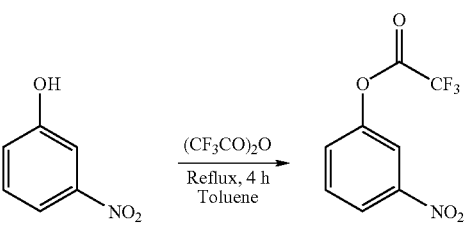 | 3-NP |
| 9.38 | 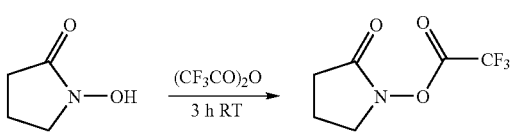 | NHP |

Example 13

General Method for the Preparation of Active Esters of N-Substituted Piperazine Acetic Acid from Trifluoroacetate Esters A solution of the trifluoroacetate in THF (0.58 M, 1.2 equiv) was added to a solid sample of N-methyl piperazine acetic acid and mixed in a vortex or shaker until a homogeneous solution was obtained. The reaction of the carboxylic acid with the trifluoroacetate ester was generally complete within 30 min for all cases except N-hydroypyrrolidinone (NHP, 18 h). The progress of conversion to the active ester was monitored by ES-MS. The amount of product and any starting material (N-MPA) could be determined by direct infusion of a sample of the reaction (in ethanol) into the ES-MS. In some cases the active ester product was precipitated as dihydrochloride salt by the addition of a solution by addition of HCl solution in dioxane (4 M, 50% volume of the reaction) followed by washing with THF, ethyl acetate and hexanes. In other cases the product was isolated from the reaction as the mono TFA salt. Addition of TFA could be performed if the bis-TFA salt was desired.

| | |
|---|---|
| Dhbt ester, Calculated MH$^+$ = 304.14 | Found = 304.20 |
| NHP ester, Calculated MH$^+$ = 242.15 | Found = 242.20 |
| 4-NP ester, Calculated MH$^+$ = 280.13 | Found = 280.20 |

$^1$H NMR (400 MHz, CDCl$_3$) d 8.20 (d, 2H, J=9.2 Hz, aromatic protons), 7.25 (d, 2H, J=9.2 Hz, aromatic protons), 3.69-3.40 (broad, 2H, ring protons), 3.57 (s, 2H, —C$\underline{H}_2$—CO—), 3.15-2.90 (broad, 6H, ring protons), 2.78 (s, 3H, —CH$_3$).

| | |
|---|---|
| Pfp ester, Calculated MH$^+$ = 325.10 | Found = 325.10 |
| Pcp ester, Calculated MH$^+$ = 404.95 | Found = 405.90 |
| 3-NP ester, Calculated MH$^+$ = 280.13 | Found = 280.20 |
| NHS ester, Calculated MH$^+$ = 256.13 | Found = 256.10 |

Example 14

Synthesis of the NHS-Ester of N-methyl Piperazine Acetic Acid-1, 2-$^{13}$C-$^{18}$O$_2$, 2HCl (the 114 Labeling Reagent)

To a slurry of N-methyl piperazine acetic acid-1,2-$^{13}$C, $^{18}$O, 2.HCl (28) (60 mg, 0.25 mmol) in THF (1.8 mL), was added DIPEA (98 mg, 0.76 mmol) under argon. The mixture was vortexed for 5 min, and the trifluoroacetate of N-hydroxysuccinimide (160 mg, 0.76 mmol) was added. After sonicating for 10 minutes, the reaction mixture was stirred at room temperature for 4 hours, followed by a centrifugation to remove any undissolved material. The supernatant was decanted then diluted with THF (3 mL) and added slowly to a 4M solution of HCl in dioxane (1.8 mL). The precipitated HCl salt of the NHS-ester was separated by centrifugation, and washed with THF (3 mL×4), dried under high vacuum to yield 62 mg (74%) of the NHS ester (30) as an off-white solid. MS (ESI, m/z) 261 (M+1), $^1$H-NMR (DMSOd$_6$) δ 4.05 (d, 1H, J=7 Hz), 3.7 (d, 1H, J=7 Hz), 3.3-3.45 (b, 2H), 2.95-3.1 (b, 2H), 2.85(s, 3H), 2.75 (m,4H).

With the exception of using a different isotopically enriched N-methyl piperazine acetic acid, the above describe procedure was followed for the production of the 115 labeling reagent (31). The analytical data for the product (31) is as follows.

MS (ESI, m/z) 261 (M+1). $^1$H-NMR (DMSOd$_6$) δ4.05(s, 1H), 3.7 (s,1H), 3.3-3.4 (b, 2H), 3.1-2.95(b, 4H), 2.85 (s, 3H), 2.75-2.80 (b, 1H), 2.7 (m, 4H).

Notes: The trifluroacetate ester reagent can be reacted with the zwitterion of N-methyl piperazine acetic acid and well as with a mono salt or bis salt (e.g. mono-HCl salt, mono-TFA salt, bis-HCl salt or bis-TFA salt) of the N-methyl piperazine acetic acid. When the bis-HCl salt was used a base such as diisoproplyethylamine (DIPEA) was added to neutralize the acid. The transesterification reaction did however apparently proceed with the bis-TFA salt of N-methyl piperazine acetic acid without the addition of base.

The examples set forth above are for illustrative purposes only and should not be viewed as a limitation on the scope of the invention.

REFERENCES 1 (a) Finkelstein, J. A.; Kruse, L. I.; Leonard, T. B. Dopamine Beta-hydroxylase Inhibitors EP 0261804-A1, 1987 (b) Rautio, J.; Nevalainen, T.; Taipale, H.; Vepsalainen, J.; Gynther, J.; Laine, K.; Jarvinen, T. Synthesis and in vitro Evaluation of Novel Morpholinyl- and m-Methylpiperazinylacyloxyalkyl Prodrugs of 2-(6-Methoxy-2-naphthyl)propionic acid (Naproxen) for Topical Drug Delivery. *J. Med. Chem.* 2000, 43, 1489-1494.

2 Nudelman, A.; McCaully, R. J.; Bell, S. C. Preparation of 1,4-Benzodiazepines. American Home Products Corp. U.S. Pat. No. 3,860,581. Jan. 14, 1975.

3 Wissner, A.; Grudzinskas, C. V. Reaction of tert-Butyldimethylsilyl Esters with Oxalyl Chloride-Dimethylformamide: Preparation of Carboxalic Acid Chlorides under Neutral Conditions. *J. Org. Chem.* 1978, 43, 3972-3974.

4 Heyes, M. P.; Markey, S. P. (180)-Quinolinic acid: its esterification without back exchange for use as internal standard in the quantification of brain and CSF quinolinic acid. *Biomedical & Environmental Mass Spectrometry*, 1988, 15, 291-293.

5 Biswas, A.; Miller, M. J. Rearrangement of N-(p-Toluenesulfonyloxy)-2-Pyrrolidinone. *Heterocycles*, 1987, 26, 2849-2851.

6 (a) Stacey, M.; Bourne, E. J.; Tatlow, J. C.; Tedder, J. M. A General Method of Esterification using Trifluoroacetic anhydride. *Nature* 1949, 164, 705. (b) Sakakibara, S. Nukai, N. A New Reagent for the p-Nitrophenylation of Amino Acids. *Bull. Chem. Soc. Jpn.* 1964, 37, 1231.

7 Krusic, P. J.; Chen, K. S.; Meakin, P.; Kochi, J. K. Electron Spin Resonance Studies of Fluoroalkyl Radicals in Solution. III. Photolysis of Perfluoroketones and Adduct Formation. *J. Phys. Chem.* 1974, 78, 2036-2047.

8 Bates, G. S.; Diakur, J.; Masamune, S. Selective and Direct Activation of O-esters. Conversion of Phenyl and 2,2,2-Trifluoroethyl Esters into Acyl Imidazolides. *Tetrahedron Letters*, 1976, 49, 4423-4426.

9 Bishop, B. F. New Antiparasitic Agents Related to the Milbemycins and Avermectins. Pfizer Ltd. WO9415944, 21 Jul. 1994.

10 Rao, T. Sudhakar; Nampalli, Satyam; Sekher, Padmanabhan; Kumar, Shiv. TFA-NHS as Bifunctional Protecting Agent: Simultaneous Protection and Activation of Amino Carboxylic Acids. *Tetrahedron Letters* 2002, 43, 7793-7795.

11 Sakakibara, Shumpei; Inukai, Noriyoshi. Trifluoroacetate Method of Peptide Synthesis. I. The Synthesis and Use of Trifluoroacetate Reagents. *Bulletin of the Chemical Society of Japan*, 1965, 38, 1979-1984.

We claim:

1. An isotopically enriched N-substituted piperazine acetic acid compound of the formula:

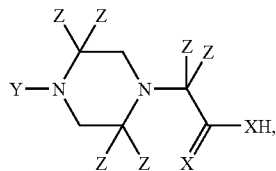

or a salt thereof, wherein;

X is O or S;

Y is a straight chain or branched C1-C6 alkyl group or a straight chain or branched C1-C6 alkyl ether group wherein the carbon atoms of the alkyl group or alkyl ether group each independently are optionally substituted with linked deuterium or fluorine atoms;

each Z is independently hydrogen, deuterium, fluorine, chlorine, bromine, iodine, an amino acid side chain, a straight chain or branched C1-C6 alkyl group that may optionally contain a substituted or unsubstituted aryl group wherein the carbon atoms of the alkyl and aryl groups each independently are optionally substituted with linked deuterium or fluorine atoms, a straight chain or branched C1-C6 alkyl ether group that may optionally contain a substituted or unsubstituted aryl group wherein the carbon atoms of the alkyl and aryl groups each independently are optionally substituted with linked deuterium or fluorine atoms or a straight chain or branched C1-C6 alkoxy group that may optionally contain a substituted or unsubstituted aryl group wherein the carbon atoms of the alkoxy and aryl groups each independently are optionally substituted with linked deuterium or fluorine atoms.

2. The compound of claim 1, wherein the N-substituted piperazine acetic acid is isotopically enriched with two or more heavy atom isotopes.

3. The compound of claim 1, wherein the N-substituted piperazine acetic acid is isotopically enriched with three or more heavy atom isotopes.

4. The compound of claim 1, wherein the N-substituted piperazine acetic acid is isotopically enriched with four or more heavy atom isotopes.

5. The compound of claim 2, wherein the heavy atom isotopes are each independently $^{18}O$, $^{15}N$ or $^{13}C$, but not deuterium.

6. The compound of claim 1, wherein each Z is independently hydrogen, fluorine, chlorine, bromine or iodine.

7. The compound of claim 1, wherein each Z is independently hydrogen, methyl or methoxy.

8. The compound of claim 1, wherein Y is methyl, ethyl, n-propyl, isopropyl, n-butyl, isobutyl, sec-butyl or tert-butyl.

9. The compound of claim 1, wherein X is $^{16}O$ or $^{18}O$.

10. The compound of claim 1, wherein each nitrogen atom of the piperazine ring is independently $^{14}N$ or $^{15}N$.

11. The compound of claim 1 of the formula:

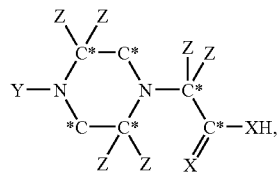

wherein, each C* is independently $^{12}C$ or $^{13}C$;

X is O or S;

Y is a straight chain or branched C1-C6 alkyl group or a straight chain or branched C1-C6 alkyl ether group wherein the carbon atoms of the alkyl group or alkyl ether group each independently are optionally substituted with linked deuterium or fluorine atoms;

each Z is independently hydrogen, deuterium, fluorine, chlorine, bromine, iodine, an amino acid side chain, a straight chain or branched C1-C6 alkyl group that may optionally contain a substituted or unsubstituted aryl group wherein the carbon atoms of the alkyl and aryl groups each independently are optionally substituted with linked deuterium or fluorine atoms, a straight chain or branched C1-C6 alkyl ether group that may optionally contain a substituted or unsubstituted aryl group wherein the carbon atoms of the alkyl and aryl groups each independently are optionally substituted with linked deuterium or fluorine atoms or a straight chain or branched C1-C6 alkoxy group that may optionally contain a substituted or unsubstituted aryl group wherein the carbon atoms of the alkyl and aryl groups each independently are optionally substituted with linked deuterium or fluorine atoms.

12. The compound of claim 1 of the formula:

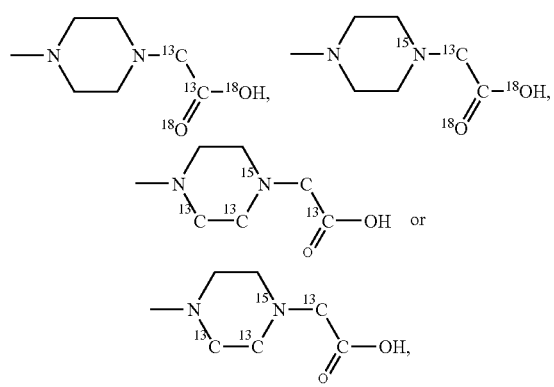

or a salt therof.

13. The compound of claim 12, wherein the compound is a zwitterion, mono-TFA salt, a mono-HCl salt, a bis-TFA salt or a bis-HCl salt.

14. The compound of claim 12, wherein each incorporated heavy atom isotope is present in at least 80 percent isotopic purity.

15. The compound of claim 12, wherein each incorporated heavy atom isotope is present in at least 93 percent isotopic purity.

16. The compound of claim 12, wherein each incorporated heavy atom isotope is present in at least 96 percent isotopic purity.

17. The compound of claim 1, wherein the N-substituted piperazine acetic acid is a mono-TFA salt, a mono-HCl salt, a bis-HCl salt or a bis-TFA salt.

18. The compound of claim 1, wherein each incorporated heavy atom isotope is present in at least 80 percent isotopic purity.

19. The compound of claim 1, wherein each incorporated heavy atom isotope is present in at least 93 percent isotopic purity.

20. The compound of claim 1, wherein each incorporated heavy atom isotope is present in at least 96 percent isotopic purity.

21. The compound of claim 12, wherein the compound is a carboxylate anion.

22. The compound of claim 1, wherein the compound is a carboxylate anion.

23. An isotopically enriched N-substituted piperazine acetic acid compound of the formula:

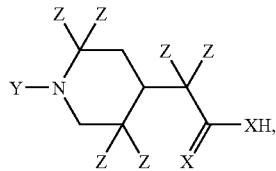

or a salt thereof, wherein;
   each X is O or S;
   Y is a straight chain or branched C1-C6 alkyl group or a straight chain or branched C1-C6 alkyl ether group wherein the carbon atoms of the alkyl group or alkyl ether group each independently are optionally substituted with linked deuterium or fluorine atoms; and
   each Z is independently hydrogen, fluorine, chlorine bromine, iodine, an amino acid side chain or a straight chain or branched C1-C6 alkyl group that may optionally contain a substituted or unsubstituted aryl group wherein the carbon atoms of the alkyl and aryl groups each independently are optionally substituted with linked fluorine atoms;

wherein the N-substituted piperazine acetic acid is isotopically enriched with one or more $^{13}C$ atoms and/or $^{15}N$ atoms.

24. The compound of claim 23, wherein Y is a straight chain or branched C1-C6 alkyl group and each Z is independently hydrogen, fluorine, chlorine, bromine, iodine, an amino acid side chain or a straight chain or branched C1-C6 alkyl group.

25. An isotopically enriched N-substituted piperazine acetic acid compound of the formula:

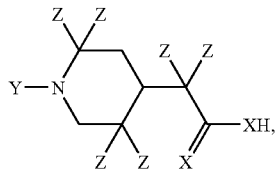

or a salt thereof, wherein;
   X is O or S;
   Y is a straight chain or branched C1-C6 alkyl group or a straight chain or branched C1-C6 alkyl ether group; and
   each Z is independently hydrogen, fluorine, chlorine, bromine, iodine, an amino acid side chain or a straight chain or branched C1-C6 alkyl group; and
wherein the N-substituted piperazine acetic acid is isotopically enriched with one or more $^{13}C$ atoms, $^{15}N$ atoms and/or $^{18}O$ atoms.

26. An isotopically enriched N-substituted piperazine acetic acid compound of the formula:

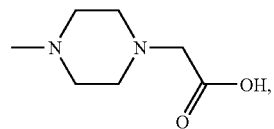

or a salt thereof, wherein the N-substituted piperazine is isotopically enriched with one or more $^{13}C$ atoms, $^{15}N$ atoms and/or $^{18}O$ atoms.

* * * * *